US005550161A

United States Patent [19]
Green

[11] Patent Number: 5,550,161
[45] Date of Patent: * Aug. 27, 1996

[54] SUBSTITUTED ORALLY EFFECTIVE ION CHELATORS RELATED TO DEFEROXAMINE

[75] Inventor: Donald E. Green, Sunnyvale, Calif.

[73] Assignee: Oral-D, Boston, Mass.

[*] Notice: The portion of the term of this patent subsequent to Jun. 9, 2004, has been disclaimed.

[21] Appl. No.: 144,664

[22] Filed: Oct. 28, 1993

Related U.S. Application Data

[63] Continuation of Ser. No. 699,610, May 13, 1991, abandoned, which is a continuation-in-part of Ser. No. 41,679, Apr. 21, 1987, Pat. No. 5,015,664, which is a continuation of Ser. No. 694,259, Jan. 26, 1985, Pat. No. 4,671,901, which is a continuation-in-part of Ser. No. 574,482, Jan. 26, 1984, Pat. No. 4,684,482.

[51] Int. Cl.⁶ ................................................. A61K 31/16
[52] U.S. Cl. .......................................... 514/616; 514/507
[58] Field of Search .......................... 564/153; 514/616, 514/507; 560/251; 562/874; 554/57

[56] References Cited

U.S. PATENT DOCUMENTS

| | | | |
|---|---|---|---|
| 3,118,823 | 1/1964 | Gaeumann et al. | 195/80 |
| 3,153,621 | 10/1964 | Gaeumann et al. | 195/80 |
| 3,247,197 | 4/1966 | Gaeumann et al. | 260/244 |
| 4,671,901 | 6/1987 | Green | 562/874 |
| 5,015,664 | 5/1991 | Green | 514/616 |
| 5,047,421 | 9/1991 | Green | 574/507 |

OTHER PUBLICATIONS

Cropper et al, Science, 511–513, 1973.
Perl et al, Science, 208, 297–299, 1980.
Alfrey et al, New Eng. Journal of Med. 294(4), 184–188, 1976.
Okarma, VAMC, Palo Alto, CA, RD15, 1983.
Grapper et al, ed. Katzman et al, vol. 7, Black Raven Press, 471–485 1978.
McDermott et al, Neurology, 29, 809–814, 1979.
Yalokowsky et al, Drug Design, Ariens Ed, 1980, 161–179.
Yamaoka et al., J. Pham. Sciences, 72(4), 400–405, 1983.
Trapp et al, Biological Psychiatry, 13(6), 708–718 (1978).
Cropper et al, Brain, 99, 67–80, 1976.
Cropper et al, Physiology & Behavior, 10, 935–945, 1973.
Bickel et al, Helv. Chim. Acta, 46, 153, 1385–1389, 1963.
Bickel et al, Helv. Chim. Acta, 43, 2778–2128, 1960.
Bickel et al, Helv. Chim. Acta, 43, 2129–2138, 1960.
Prelog et al, Helv. Chim Acta, 45, 631–637, 1962.

Green et al, 186th Annual Am. Chem. Soc. Meeting, 1983, Abstract No. MEDI 56.
Weatherall et al, New. Eng. J. of Med., 308(8) 456–457, 1983.
Okarma, VAMC, Palo Alto, CA RD15, 1982.

Primary Examiner—Shailendra Kumar
Attorney, Agent, or Firm—Heller, Ehrman, White & McAuliffe

[57] ABSTRACT

Compounds are described of the general formula:

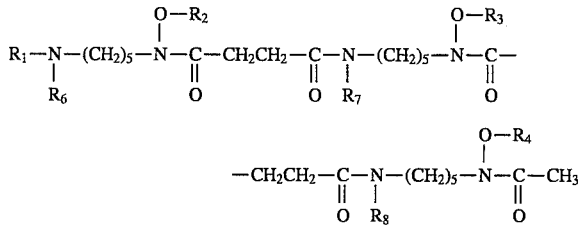

wherein:

$R_1$ is acyl of the formula $-C(=O)-R_5$: $R_2$, $R_3$, $R_4$, $R_6$, $R_7$ and $R_8$ are each selected from the group consisting of hydrogen and acyl of the formula:
$-C(=O)-R_5$
wherein $R_5$ is selected from the group consisting of alkyls, substituted alkyls, alkenyls, substituted alkenyls, cycloalkyls, substituted cycloalkyls, arylalkylenes, substituted arylalkylenes, alkylenecycloalkyls, alkylene substituted cycloalkyls, alkynyls, substituted alkynyls, aryls and substituted aryls, wherein $R_2$, $R_3$ and $R_4$ are selected such that at least one of $R_2$, $R_3$ and $R_4$ is an acyl.

When $R_2$, $R_3$ and $R_4$ include one or more acyls that are not identical to the acyl of $R_1$, these compounds of formula I are novel compounds. The invention also includes processes to produce the compounds of formula I.

Compounds of formula I complex and/or chelate tissue tri-valent ions, especially iron and aluminum ($Fe^{+++}$, $Al^{+++}$), when administered to a human being, and are therefore useful in therapy in the treatment of diseases in which tissue ion levels in the body have increased or toxic levels. These iron-related diseases include, for example, thalassemia major, sideroachrestic anemic, BlacKfan-Diamond anemia, aplastic anemia, sickle cell anemia, hemolytic anemias and hemosiderosis brought about by multiple blood transfusions including treatment for the anemia accompanying conditions requiring kidney dialysis. Aluminum-related diseases or conditions include Alzheimer's disease, senile dementia and dialysis encephalopathy.

15 Claims, 2 Drawing Sheets

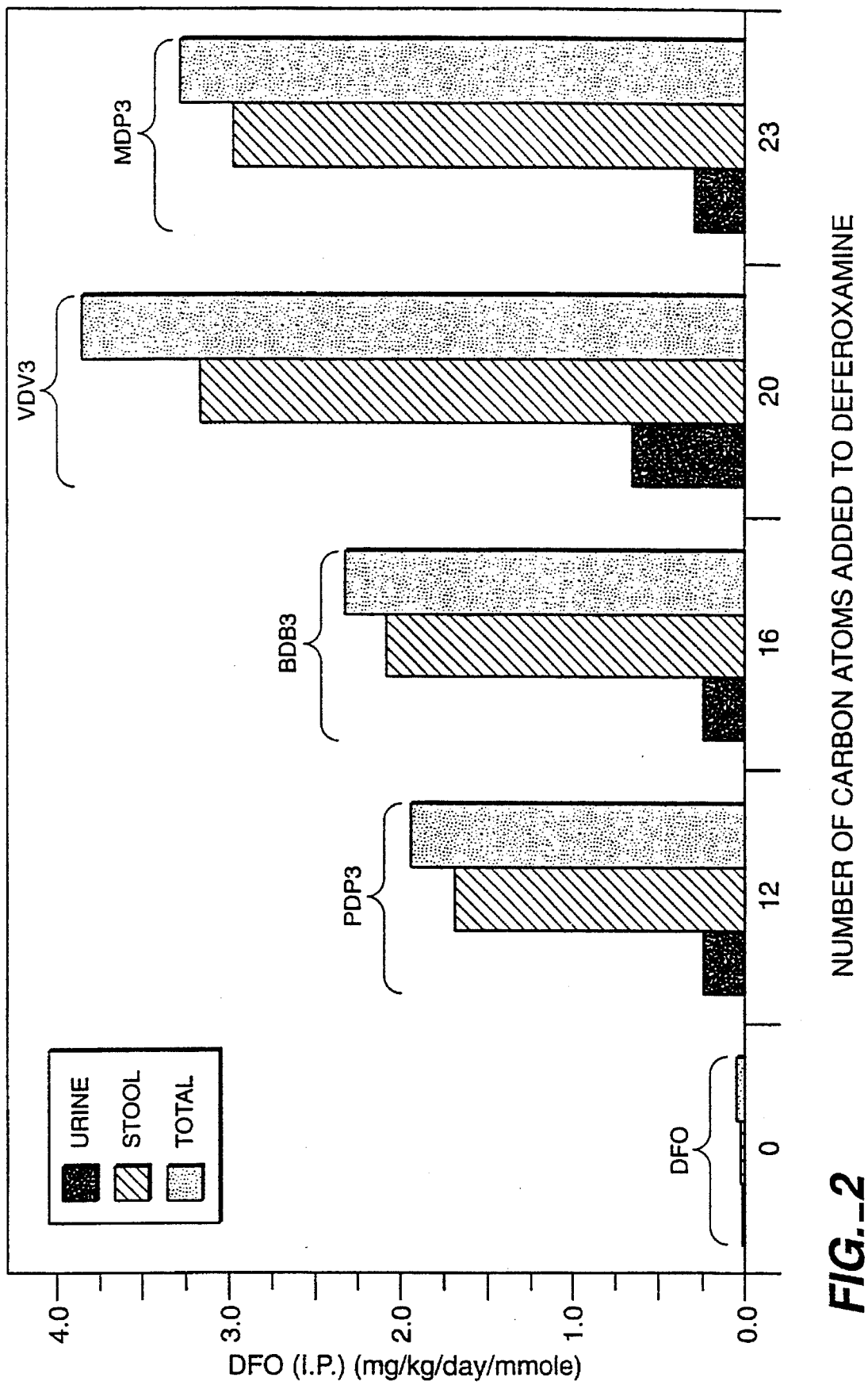
FIG._2

SUBSTITUTED ORALLY EFFECTIVE ION CHELATORS RELATED TO DEFEROXAMINE

This is a continuation of application Ser. No. 07/699,610, filed on May 13, 1991, abandoned, which is a continuation-in-part of U.S. Ser. No. 041,679, filed Apr. 21, 1987, now U.S. Pat. No. 5,015,664, which is a continuation of Ser. No. 694,259, filed Jan. 26, 1985, now U.S. Pat. No. 4,671,901, which is a continuation-in-part of U.S. Ser. No. 574,482, filed Jan. 26, 1984, now U.S. Pat. No. 4,684,482.

FIELD OF THE INVENTION

The present invention is concerned with the preparation of compounds, compositions and methods which are useful for treating diseases in human beings which are a result of a body tri-valent ion (i.e. $Fe^{+++}$, $Al^{+++}$) overload state.

BACKGROUND OF THE INVENTION

Iron overload diseases include thalassemia major, sideroachrestic anemia, Blackfan-Diamond anemia, aplastic anemia, sickle cell anemia, other hemolytic anemias, and a number of other diseases and conditions in which hemosiderosis (a focal or general increase in tissue iron stores without associated tissue damage) occurs. One type of hemosiderosis occurs in most patients after multiple blood transfusions have occurred. Another type of hemosiderosis occurs as the result of the treatment of an anemia found in kidney damaged patients where dialysis is used to remove toxic wastes. Treatment of these conditions has generally involved the administration of a chelating agent having a selective affinity for tissue $Fe^{+++}$ ion which can then be excreted as the iron chelate.

The ideal chelating agent for the reduction of tissue metal ions, e.g. iron, aluminum, gallium, ytterbium, indium and the like should have at least the following attributes:

1. Have high selectivity with respect to ion, e.g. iron, binding;
2. Be essentially metabolically inert;
3. Be essentially non-toxic;
4. Be inexpensive to produce; and
5. Be capable of oral administration.

Over the years a number of approaches have been investigated which have some of these attributes. The current drug of choice is deferoxamine, a compound obtained from the microorganism *streptomyces pilosus*. Deferoxamine has the following structure:

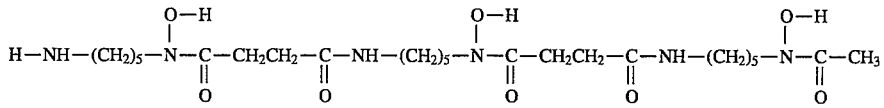

This material meets the aforementioned criteria except for oral availability. Deferoxamine (as the methanesulfonate salt) has been shown to be most effective when it is delivered parenterally via slow continuous (about an 8–12 hour period) subcutaneous infusion using a portable infusion pump, i.e., a battery powered syringe pump.

This administration route for iron overload conditions is particularly difficult in view of the widespread occurrance of the disease, thalassemia major, found in the population in countries bordering on the Mediterranean Sea and extending eastward through the Middle East, India to Southeast Asia, and in sickle cell anemia which is prevalent in the populations in Africa.

The present invention concerns certain acyl derivatives of deferoxamine which are effective ion, e.g. iron, aluminum, etc. chelators when administered orally.

Some compounds related to the compounds of the present invention are described in the literature by H. Bickel, et al. in *Helvitica Chimica Acta*, Vol. 46, No. 153, pp 1385–1389, published in 1963 and their related U.S. Patent No. 3,247,197, both of which are incorporated herein by reference.

The focus of these references are the preparation of N-acyl trihydroxy derivatives of deferoxamine which have the structure:

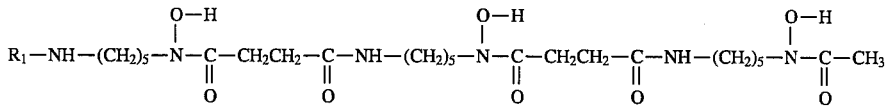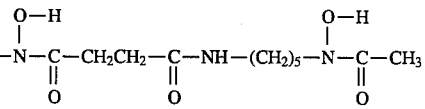

wherein $R_1$ may be an acyl group. These references mention tetra acyl materials, i.e., materials of the formula:

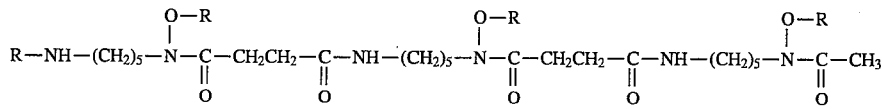

wherein the R groups are each acetyls, as intermediates in the production of their focus compounds. These references do not teach the use of tetra-acyl materials in body ion, e.g., iron, removal applications nor do they suggest that the tetra- or higher acyl materials either as pure isomers or as mixtures would be effective when orally administered in these applications.

Deferoxamine mesylate [DESFERAL$^R$/Ciba-Geigy] (DFO) as an intraperitoneally administered iron-chelating agent is successfully marketed to facilitate the removal of iron in the treatment of acute iron intoxication and/or in chronic iron overload due to transfusion-dependent anemias and other related disease conditions.

U.S. Pat. Nos. 3,118,823 and 3,153,621 are concerned with iron chelates of deferoxamine, which are used as growth factors. Additional references of interest in this art include Bickel, et al., Helvitica Chimica Acta, Vol. 43, pp. 2118 ff and 2129 ff, published in 1960; and V. Prelog and Walser, Helvitica Chimica Acta, Vol. 45, pp 631 ff, published in 1962. Finally, D. E. Green and T. B. Okarma briefly reported on studies on the preparation of some tetra-acyl derivatives of deferoxamine and the biological properties of these derivatives. (See Abstracts, 186th Annual American Chemical Society Meeting, Aug. 28–Sep. 2, 1983, Washington, D.C., Abstract No. MEDI 56.

SUMMARY OF THE INVENTION

The present invention concerns a group of di-, tri-, tetra-, penta-, hexa- and hepta-acylated derivatives of deferoxamine, which are useful in the treatment of the diseases or conditions cited earlier. The invention is particularly useful in that its compounds are orally administered, absorbed from the digestive system into the body and cleaved to produce deferoxamine in the body.

In one aspect, this invention relates to compounds of the general formula:

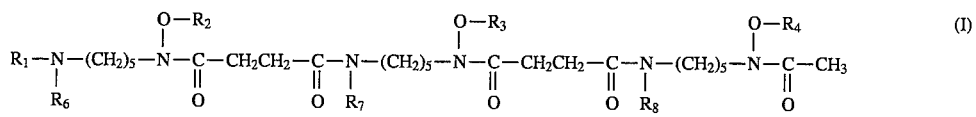

wherein:

$R_1$ is an acyl of the formula $—(C=O)-R_5$;

$R_2$, $R_3$, $R_4$, $R_6$, $R_7$ and $R_8$ are each selected from the group consisting of hydrogen and acyls of the formula:

$—C(=O)-R_5$ wherein $R_5$ is independently selected for each from the group consisting of alkyls, substituted alkyls, alkenyls, substituted alkenyls, cycloalkyls, substituted cycloalkyls, arylalkylenes, substituted arylalkylenes, alkylenecycloalkyls, alkylene substituted cycloalkyls, alkynyls, substituted alkynyls, aryls and substituted aryls.

$R_2$, $R_3$, $R_4$, $R_6$, $R_7$ and $R_8$ are selected such that at least one of $R_2$, $R_3$, $R_4$, $R_6$, $R_7$ and $R_8$ is an acyl of the formula $—C(=O)-R_5$ different than $R_1$.

When $R_2$, $R_3$, $R_4$, $R_6$, $R_7$ and $R_8$ include one or more acyls of formula $—C(=O)-R_5$, wherein $R_5$ is not identical to the $R_5$ of the acyl of $R_1$, these compounds of formula I are novel compounds and represent another aspect of this invention.

Compounds of formula I are prodrug forms of deferoxamine which liberate deferoxamine in the body to complex and/or chelate ions, such as iron and/or aluminum, for subsequent excretion when administered to a human being, and are therefore useful in therapy in the treatment of diseases in which ion, e.g. iron, aluminum, levels in the body have elevated or toxic levels. These diseases for iron overload include, for example, thalassemia major, sideroachrestic anemia, Blackfan-Diamond anemia, aplastic anemia, sickle cell anemia, hemolytic anemias and hemosiderosis brought about by multiple blood transfusions or such condition when brought about by treatment of an anemia found in kidney-damaged patients undergoing renal dialysis.

Another aspect of the present invention relates to compounds of formula I as is described herein which liberate deferoxamine in the body to generally chelate any trivalent metal, such as iron, aluminum, chromium, gallium, ytterbium, indium and the like, for subsequent excretion, which is useful in the treatment of conditions (which is equivalent to diseases) in which the elevated levels of metal ion in the body cause or exacerbate disease conditions. The compounds of formula I are useful as oral pharmaceuticals in the treatment of Alzheimer's and related diseases in which elevated aluminum levels have been found in the body, particularly the brain. Diseases or conditions having elevated aluminum body levels also include senile dementia and dialysis encephalopathy.

Thus other aspects of the invention concern pharmaceutical preparations incorporating the compounds of formula I, dosage forms thereof and methods of treatment of the aforementioned conditions employing these preparations and/or dosage forms.

Another aspect of this invention is a process for the preparation of the compounds of formula I, as is described in greater detail hereinafter.

DESCRIPTION OF THE FIGURES

FIG. 2 shows a graphic comparison of iron excretion in response to deferoxamine derivatives adminsistered orally.

DETAILED DESCRIPTION OF THE INVENTION

Definitions

Figure 1:
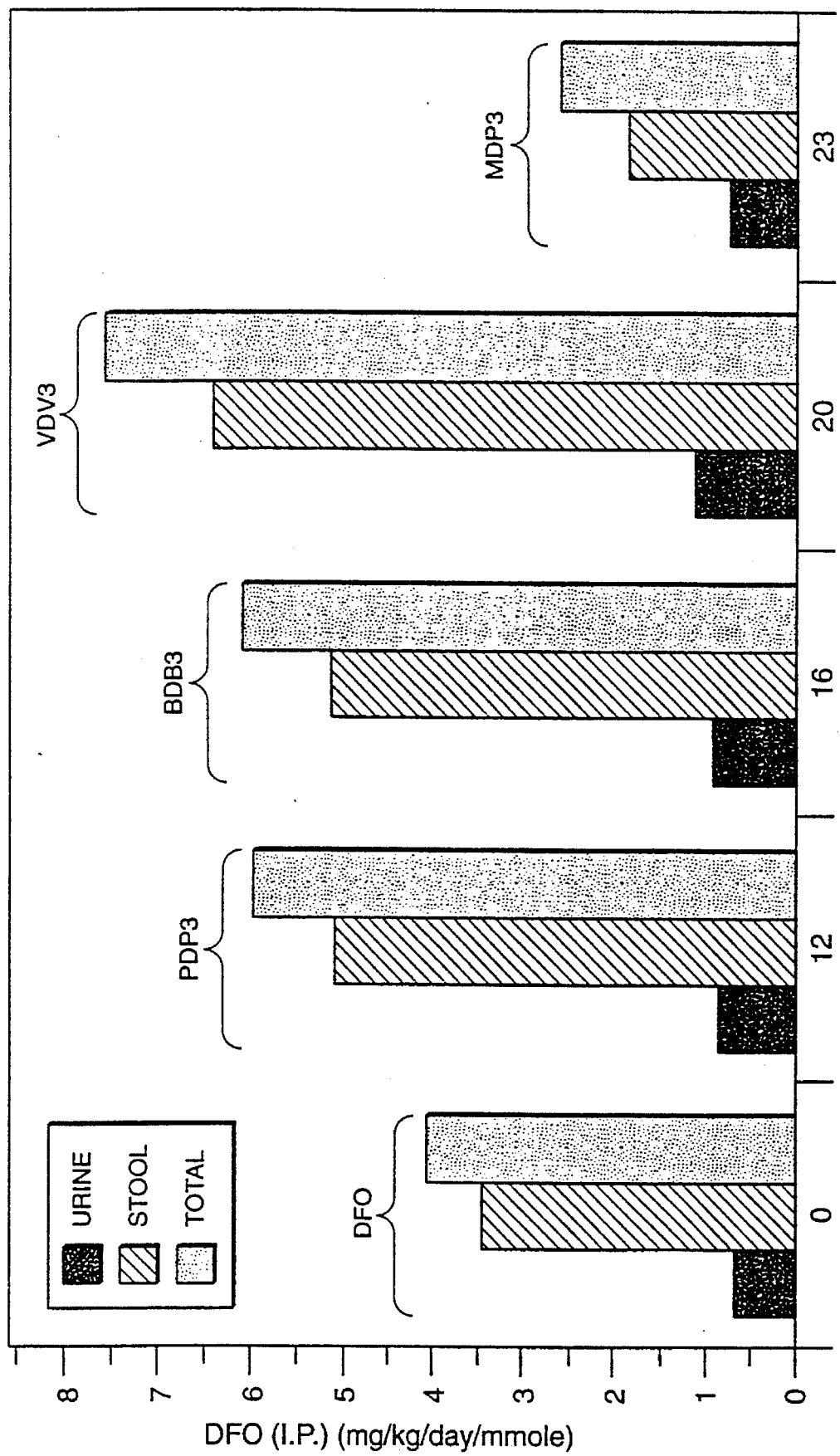
FIG. 1 shows a comparison of iron excretion in response to deferoxamine derivatives administered intraperitoneally.

"Acyl" is defined to refer to a group having the structure, $—(C=O)-R_5$, wherein $R_5$ is selected from the group consisting of alkyls, substituted alkyls, alkenyls, substituted alkenyls, cycloalkyls, substituted cycloalkyls, arylalkylenes, substituted arylalkylenes, alkylenecycloalkyls, alkylene substituted cycloalkyls, alkynyls, substituted alkynyls, aryls and substituted aryls.

"Acylating agent" refers to a compound containing the group —(C=O)-$R_5$ which can react and insert an "acyl" into deferoxamine. Representative agents include, for example, acyl halides, acyl anhydrides, mixed acyl anhydrides and mixtures thereof. When different acylating agents are employed herein they may include acylating agents which are in different catagories, e.g., alkyl acyl (acetyl chloride) and alkenyl acyl (methacryloyl chloride) or may include different acylating agents within the same category (e.g., acetyl chloride and propionyl chloride, etc.) or by substitution of one to three protons, e.g., propionyl chloride and 2-chloropropionyl chloride.

"Alkyl" refers to a branched or unbranched saturated hydrocarbon containing 1 to 25 carbon atoms, such as, for example, methyl, ethyl, n-propyl, i-propyl, n-butyl, i-butyl, s-butyl, t-butyl, n-heptyl, i-heptyl, n-octyl, nonyl, decyl, undecyl, tridecyl, pentadecyl, heptadecyl, pentacosanyl and the like.

"Substituted alkyl" refers to an "alkyl" group, wherein at positions on the linear or branched structure one to three protons have been replaced by a group such as alkoxyl or halogen.

"Alkenyl" refers to a linear or branched unsaturated hydrocarbon group containing from 2 to 25 carbon atoms, such as, for example, ethenyl, propenyl, butenyl (1- and 2-), isobutenyl, hexenyl, heptenyl, nonenyl, undecenyl, dodecenyl, nonadecenyl, cosenyl, pentacosenyl and the like.

"Substituted alkenyl" refers to an "alkenyl" where at positions on the linear or branched structure, one to three protons have been replaced by a group such as alkoxyl or halogen.

"Cycloalkyl" refers to a cyclic alkyl structure containing 3 to 25 carbon atoms. The cyclic structure may have alkyl substituents at any position. Representative groups include cyclopropyl, 4-methylcyclohexyl, cyclooctyl, cyclohexadecyl, cyclopentacosanyl and the like.

"Substituted cycloalkyl" refers to a "cycloalkyl" where at positions on the group, one to three protons have been replaced by a group, such as alkoxyl, alkyl or halogen.

"Arylalkylene" refers to a group containing an "aryl" attached through an "alkylene." Representative groups include benzyl (phenylmethylene), phenylethylene (phenethyl), phenyldecylene, naphthylmethylene, naphthyl-2-methylethylene and the like.

"Substituted arylalkylene" refers to an "arylalkylene" containing a "substituted aryl" moiety. Representative groups include 2-methylphenylmethylene, 4-chlorophenylethylene, 4-bromophenylpropylene, 6-methoxynephthylmethylene, 6-chloronaphthyldecylene and the like.

"Alkylenecycloalkyl" refers to a group wherein the alkylene portion is a saturated hydrocarbon which contains 1 to 10 carbon atoms. One end of which is attached to the —C(=O)— group and the other end of which is attached to a "cycloalkyl" group. Representative groups include ethylenecyclopropyl, propylenecyclohexyl, 2-methylpropylenecyclodecyl, decylenecyclopentacosanyl and the like.

"Alkylene substituted cycloalkyl" refers to an alkylenecycloalkyl having a "substituted cycloalkyl" moiety. Representative groups include methylene-2-chlorocyclopropyl, ethylene-4-methylcyclohexyl, decylene-4-hydroxycyclodecyl, decylene-2-bromocyclopentacosanyl and the like.

"Alkynyl" refers to a branched or linear aliphatic hydrocarbon group having a —C≡C— moiety which contains from 2 to 25 carbon atoms, such as for example, ethynyl, propynyl, isohexynyl, heptynyl, pentadecynyl, pentacosynyl and the like.

"Substituted alkynyl" refers to an "alkynyl" group, where at positions on the linear or branched structure, one to three protons have been replaced by a group such as alkoxy or halogen.

"Halo" or "halogen" refers to fluoro, chloro, bromo or iodo, usually as a substitutent replacing a hydrogen atom in an organic group.

"Alkylene" refers to a saturated linear or branched hydrocarbon structure containing 1 to 10 carbon atoms which has two points of attachment to other functional groups. Representative "alkylenes" include methylene (—$CH_2$—), ethylene (—$CH_2$-$CH_2$—), 2-methylpropylene [—$CH_2$-CH($CH_3$)-$CH_2$—], hexylene, decylene and the like.

"Aryl" refers to a carbon-containing aromatic structure having 6 to 14 carbon atoms. Representative groups include phenyl, naphthyl, phenanthryl and the like.

"Substituted aryl" refers to an "aryl" wherein at 1 to 3 positions on the aromatic ring, one to three protons have been replaced by another group, such as alkyl, alkoxyl or halogen.

The compounds of this present invention are generally named according to the IUPAC or *Chemical Abstracts* nomenclature. Thus, deferoxamine may be named N'-[5-[[4-[[-5-(acetylhydroxamino) pentyl]amino]-1,4-dioxobutyl]hydroxyamino]pentyl]-N-( 5-aminopentyl)-N-hydroxybutanediamide; or N-[5-[3-[(5-aminopentyl)hydroxylcarbamoyl]propionamido]-pentyl]- 3-[[5-(N-hydroxyacetamido)pentyl]-carbamoyl]propionohydroxamic acid; or 1-amino-6,17-dihydroxy-7, 10,18,21-tetraoxo-27-(N-acetylhydroxylamino)-6,11,17,22-tetraazaheptaeicosane.

Because of the obvious complexity of the names for the substituted structures of deferoxamine, a shorthand form based upon the last written name above is used for the present invention. Therefore, the 1-amino group, when substituted by acyl ($R_1$-), is designated as N-acyl (-N-$R_1$). The hydroxamic acid hydrogen at the 6-position, when substituted by acyl ($R_2$-) is designated as O-acyl (-O-$R_2$). The hydroxamic acid hydrogen at the 17-position, when substituted by acyl ($R_3$-) is designated as O-acyl (-O-$R_3$). And the hydroxamic acid hydrogen of the "27-(N-acetylhydroxylamino)" when substituted by acyl ($R_4$-) is designated as (-O-$R_4$). The second hydrogen on the 1-amino group and the hydrogens on the amide nitrogens at the 11 and 22 positions, when substituted by acyl, are also N-acyls designated by $R_6$(-N-$R_6$), $R_7$(-N-$R_7$) and $R_8$(-N-$R_8$), respectively.

Thus in formula I, when $R_1$ is acetyl, and $R_2$, $R_3$, and $R_4$ are each n-octanoyl, the compound name is N-acetyl-O,O,O-trioctanoyldeferoxamine. When $R_1$ is isovaleryl, $R_2$ is acetyl (i.e., $R_5$ here is —$CH_3$), $R_3$ is butyryl ($R_5$ here is —$CH_2CH_2CH_3$) and $R_4$ is n-octanoyl [$R_5$ here is —$CH_2(CH_2)_5CH_3$], the compound name is N-isovaleryl-O,O,O-acetylbutyryl-n-octanoyldeferoxamine. If the amino group or any combination of the hydroxamic acid groups are unsubstituted, the unsubstituted position is designated as N-hydrogen (N-H) or -O-hydrogen (-O-H), respectively, reading $R_2$, $R_3$, and $R_4$, from left to right for the compound of formula I. In the compound when $R_1$ is acetyl, $R_2$, $R_3$, $R_4$, and $R_6$ are each octanoyl and $R_7$ and $R_8$ are H, the compound is named N-acetyl-O,O,O,N,H,H-tetraoctanoyldeferoxamine.

In defining the size of organic groups, i.e., $R_5$- herein, "lower" groups (e.g., lower alkyl) contain 1 to 7 carbon atoms, "intermediate" groups (e.g., intermediate alkenyl) contain 8 to 15 carbon atoms, and "higher" groups (e.g., higher alkyl) contain from 16 to 25 carbon atoms.

DETAILED DESCRIPTION AND PRESENTLY PREFERRED EMBODIMENTS

Although not understood with certainty, it appears that the best results are obtained when the total number of carbon atoms in the groups $R_1$, $R_2$, $R_3$, $R_4$, $R_6$, $R_7$ and $R_8$ of formula I is between 10 and 60, preferably between 12 and 40, and especially between 14 and 30. Structures of formula I where the total of the carbon atoms in the groups $R_1$, $R_2$, $R_3$, $R_4$, $R_6$, $R_7$ and $R_8$ are less than 9 have not yet achieved good results, perhaps because deferoxamine derivatives having these smaller acyls are not sufficiently absorbed through the membranes of the digestive tract. Structures of formula I wherein the total of the carbon atoms of $R_1$, $R_2$, $R_3$, $R_4$, $R_6$, $R_7$ and $R_8$ is greater than 63 have not yet achieved good results, perhaps because the molecules are not sufficiently soluble in the fluids within the digestive tract to be absorbed into the body as the prodrug to be cleaved to produce deferoxamine.

The compounds of formula I, prepared according to the procedures described herein and which achieve good results in reducing the amount of tissue iron or aluminum in a human being, are found in Table I.

TABLE I

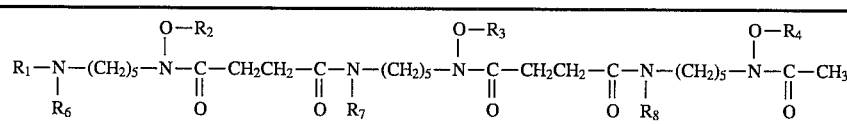

DEFEROXAMINE DERIVATIVES

| Compound Group | Number of Carbon Atoms | | | | | | |
|---|---|---|---|---|---|---|---|
| | $R_1$ | $R_2$ | $R_3$ | $R_4$ | $R_6$ | $R_7$ | $R_8$ |
| 1 | 2 | 3 | 3 | 3 | 0 | 0 | 0 |
| 1A | 2 | 2 | 2 | 2 | 2 | 0 | 0 |
| 1B | 2 | 2 | 2 | 2 | 2 | 0 | 2 |
| 1C | 2 | 2 | 2 | 2 | 2 | 2 | 2 |
| 2 | 2 | 4 | 4 | 4 | 0 | 0 | 0 |
| 3 | 2 | 5 | 5 | 5 | 0 | 0 | 0 |
| 4 | 2 | 6 | 6 | 6 | 0 | 0 | 0 |
| 5 | 2 | 7 | 7 | 7 | 0 | 0 | 0 |
| 6 | 2 | 8 | 8 | 8 | 0 | 0 | 0 |
| 6A | 2 | 8 | 8 | 8 | 8 | 0 | 0 |
| 6B | 2 | 8 | 8 | 8 | 0 | 0 | 8 |
| 6C | 2 | 8 | 8 | 8 | 8 | 0 | 8 |
| 6D | 2 | 8 | 8 | 8 | 8 | 8 | 8 |
| 7 | 3 | 3 | 3 | 3 | 0 | 0 | 0 |
| 8 | 3 | 4 | 4 | 4 | 0 | 0 | 0 |
| 9 | 3 | 5 | 5 | 5 | 0 | 0 | 0 |
| 10 | 3 | 6 | 6 | 6 | 0 | 0 | 0 |
| 11 | 3 | 8 | 8 | 8 | 0 | 0 | 0 |
| 12 | 4 | 3 | 3 | 3 | 0 | 0 | 0 |
| 13 | 4 | 4 | 4 | 4 | 0 | 0 | 0 |
| 14 | 4 | 5 | 5 | 5 | 0 | 0 | 0 |
| 15 | 4 | 6 | 6 | 6 | 0 | 0 | 0 |
| 16 | 4 | 8 | 8 | 8 | 0 | 0 | 0 |
| 17 | 5 | 3 | 3 | 3 | 0 | 0 | 0 |
| 18 | 5 | 4 | 4 | 4 | 0 | 0 | 0 |
| 19 | 5 | 5 | 5 | 5 | 0 | 0 | 0 |
| 20 | 5 | 6 | 6 | 6 | 0 | 0 | 0 |
| 21 | 5 | 8 | 8 | 8 | 0 | 0 | 0 |
| 22 | 6 | 3 | 3 | 3 | 0 | 0 | 0 |
| 23 | 6 | 4 | 4 | 4 | 0 | 0 | 0 |
| 24 | 6 | 5 | 5 | 5 | 0 | 0 | 0 |
| 25A | 6 | 5 | 5 | 5 | 5 | 0 | 0 |
| 26 | 6 | 6 | 6 | 6 | 0 | 0 | 0 |
| 27 | 6 | 8 | 8 | 8 | 0 | 0 | 0 |
| 28 | 7 | 3 | 3 | 3 | 0 | 0 | 0 |
| 29 | 7 | 4 | 4 | 4 | 0 | 0 | 0 |
| 30 | 7 | 5 | 5 | 5 | 0 | 0 | 0 |
| 31 | 7 | 6 | 6 | 6 | 0 | 0 | 0 |
| 32 | 7 | 7 | 7 | 7 | 0 | 0 | 0 |
| 33 | 8 | 3 | 3 | 3 | 0 | 0 | 0 |
| 34 | 8 | 4 | 4 | 4 | 0 | 0 | 0 |
| 35 | 8 | 5 | 5 | 5 | 0 | 0 | 0 |
| 36 | 8 | 6 | 6 | 6 | 0 | 0 | 0 |
| 37 | 8 | 8 | 8 | 8 | 0 | 0 | 0 |
| 37A | 8 | 8 | 8 | 8 | 8 | 0 | 0 |
| 37B | 8 | 8 | 8 | 8 | 8 | 0 | 8 |
| 37C | 8 | 8 | 8 | 8 | 8 | 8 | 8 |

Preferred compounds of formula I found in the "Compound Groups" in Table I are those compounds wherein in $R_1$, $R_5$ is alkyl, and $R_2$, $R_3$, $R_4$, $R_6$, $R_7$ and $R_8$ are independently selected from hydrogen or acyl of the formula —(C=O)-$R_5$, where $R_5$ is independently selected for each from alkyl groups. More preferred are the lower alkyl groups. Especially preferred are those compounds where $R_6$, $R_7$ and $R_8$ are hydrogen. Preferred compounds are those wherein $R_6$, $R_7$ and $R_8$ are hydrogen. Preferred groups include Compound Groups 1A, 7, 13, 19, 26, 32, 37, 37A, 37B and 37C wherein $R_1$, $R_2$, $R_3$, $R_4$, $R_6$, $R_7$ and $R_8$ each contain the same number of carbon atoms or hydrogen. More preferred are those groups wherein $R_5$ is alkyl, particularly lower alkyl and especially where $R_5$ is the same alkyl group. These compounds where $R_5$ is alkyl are preferred to be orally administered to treat the iron and aluminum related diseases described herein.

Preferred compounds of formula I also include those wherein up to five of $R_2$, $R_3$, $R_4$, $R_6$, $R_7$ and $R_8$ are hydrogen, more preferably the hydrogens are found on positions $R_6$, $R_7$ and $R_8$. See, for example, Table II.

TABLE II $$R_1-N(R_6)-(CH_2)_5-N-C(=O)-CH_2CH_2-C(=O)-N(R_7)-(CH_2)_5-N-C(=O)-CH_2CH_2-C(=O)-N(R_8)-(CH_2)_5-N-C(=O)-CH_3$$

with $O-R_2$, $O-R_3$, $O-R_4$ substituents.

DEFEROXAMINE DERIVATIVES

| Compound Group | Number of Carbon Atoms[a] | | | | | | |
|---|---|---|---|---|---|---|---|
| | $R_1$ | $R_2$ | $R_3$ | $R_4$ | $R_6$ | $R_7$ | $R_8$ |
| 1 | 2 | 8 | 8 | 0 | 0 | 0 | 0 |
| 1A | 2 | 8 | 8 | 0 | 8 | 0 | 0 |
| 1B | 2 | 8 | 8 | 0 | 8 | 0 | 8 |
| 2 | 2 | 8 | 0 | 8 | 0 | 0 | 0 |
| 3 | 2 | 0 | 8 | 8 | 0 | 0 | 0 |
| 4 | 2 | 0 | 0 | 8 | 0 | 0 | 0 |
| 5 | 2 | 0 | 8 | 0 | 0 | 0 | 0 |
| 6 | 2 | 8 | 0 | 0 | 0 | 0 | 0 |
| 7 | 4 | 4 | 4 | 0 | 0 | 0 | 0 |
| 8 | 4 | 6 | 0 | 6 | 0 | 0 | 0 |
| 9 | 4 | 0 | 8 | 8 | 0 | 0 | 0 |
| 10 | 5 | 5 | 5 | 0 | 0 | 0 | 0 |
| 11 | 5 | 0 | 6 | 6 | 0 | 0 | 0 |
| 12 | 6 | 6 | 6 | 0 | 0 | 0 | 0 |
| 13 | 6 | 5 | 5 | 0 | 0 | 0 | 0 |
| 14 | 6 | 8 | 8 | 0 | 0 | 0 | 0 |
| 15 | 8 | 8 | 8 | 0 | 0 | 0 | 0 |
| 16 | 8 | 8 | 0 | 8 | 0 | 0 | 0 |
| 17 | 8 | 0 | 8 | 8 | 0 | 0 | 0 |
| 17A | 8 | 8 | 0 | 8 | 8 | 8 | 0 |
| 17B | 8 | 8 | 8 | 0 | 8 | 0 | 8 |
| 17C | 8 | 8 | 0 | 8 | 8 | 0 | 0 |
| 18 | 8 | 4 | 4 | 0 | 0 | 0 | 0 |
| 19 | 8 | 5 | 5 | 0 | 0 | 0 | 0 |
| 20 | 8 | 6 | 6 | 0 | 0 | 0 | 0 |
| 20A | 8 | 6 | 6 | 0 | 6 | 0 | 0 |
| 20B | 8 | 6 | 0 | 6 | 6 | 0 | 6 |
| 21 | 6 | 4 | 0 | 4 | 0 | 0 | 0 |
| 22 | 5 | 4 | 0 | 4 | 0 | 0 | 0 |
| 23 | 4 | 5 | 0 | 5 | 0 | 0 | 0 |
| 24 | 3 | 3 | 3 | 0 | 0 | 0 | 0 |
| 25 | 3 | 4 | 4 | 0 | 0 | 0 | 0 |
| 26 | 3 | 5 | 0 | 5 | 0 | 0 | 0 |
| 27 | 3 | 4 | 0 | 4 | 0 | 0 | 0 |
| 28 | 2 | 4 | 0 | 4 | 0 | 0 | 0 |
| 29 | 2 | 5 | 5 | 0 | 0 | 0 | 0 |
| 30 | 2 | 6 | 0 | 6 | 0 | 0 | 0 |

[a]When the carbon atom number is 0, the group $R_2$, $R_3$, $R_4$, $R_6$, $R_7$ and $R_8$ contains 0 carbon atoms, and is a hydrogen (—H).

Because of the present difficulty of separating some of the isomers of the products described in Table I and Table II, this invention includes mixtures of compounds which would normally be expected in the reaction products described in the examples below. For instance, if an excess of acylating agent is used as shown in Table I, then a mixture of compounds such as 6, 6A, 6B, 6C and 6D may be present. If in the Compound Group in Table II, numbers 15, 16, 17, 17A, 17B and 17C are present as reaction products of the acylation of deferoxamine using a limited amount of $R_1$=8 [(i.e., $R_5$=7 carbon atoms) acylating agent], then the mixture of isomers may be used in therapy. These mixtures of isomers may be separated by, e.g. high pressure liquid chromatography or may be used in a pharmaceutical composition or method of treatment as a mixture of 2 or more isomers.

Presently preferred embodiments of the present invention as a oral pharmaceutical compositions and method of treatment, include those compounds of formula I wherein $R_1$, $R_2$, $R_3$, $R_4$, $R_6$, $R_7$ and $R_8$ are hydrogen or identical alkyl acyl groups, especially lower alkyl acyls. Especially preferred are those compounds where acyl is —C(=O)-$R_5$, and $R_5$ is n-propyl, n-butyl, t-butyl, n-pentyl, n-hexyl or n-heptyl.

Another embodiment of the present invention includes those compounds of formula I as described herein, except that when $R_1$ is acyl of formula —C(=O)-$R_5$ and $R_5$ is alkyl, $R_2$, $R_3$, $R_4$, $R_6$, $R_7$ and $R_8$ as a group are hydrogen or are not each an acyl of formula —C(=O)-$R_5$ wherein $R_5$ is the identical alkyl of $R_1$.

A preferred compound is where $R_1$ is acetyl, $R_2$, $R_3$ and $R_4$ are each acyl where $R_5$ is n-heptyl; and two of $R_6$, $R_7$ and $R_8$ are hydrogen and the other is acyl where $R_5$ is n-heptyl.

Another embodiment of the present invention includes those compounds of formula I as described herein, except that when $R_1$ is acyl of formula —C(=O)-$R_5$ and $R_5$ is alkenyl, $R_2$, $R_3$, $R_4$, $R_6$, $R_7$ and $R_8$ as a group are not each acyl of formula —C(=O)-$R_5$ wherein $R_5$ is the identical alkenyl of $R_1$.

Especially preferred embodiments of the present invention also include those compounds of formula I wherein $R_1$ is acetyl and $R_2$, $R_3$, $R_4$, $R_6$, $R_7$ and $R_8$ are independently selected from hydrogen and acyl: —(C=O)-$R_5$, wherein each $R_5$ is alkyl, particularly lower alkyl, especially propyl, i-butyl, t-butyl or n-heptyl.

Additional preferred embodiments include those compounds of formula I wherein $R_1$ is —C(=O)-$R_5$ wherein $R_5$ is intermediate alkyl, and $R_2$, $R_3$, and $R_4$ are —C(=O)-$R_5$ wherein $R_5$ in each is lower alkyl. A particularly preferred embodiment is the compound where $R_1$ is —(C=O)-$R_5$ and $R_5$ is undecyl, and $R_2$, $R_3$, and $R_4$ are each —C(=O)-$R_5$ wherein $R_5$ is propyl.

Preferred compounds of the embodiments of formula I described above for a pharmaceutical composition and for a method of treatment of ion, e.g. iron or aluminum, overload diseases are those where R6, R7 and R8 are each hydrogen.

An additional embodiment of the present invention describes a pharmaceutical composition useful for treating one or more diseases or conditions in a human being, related to excess iron in the blood and/or tissue, which comprises using a therapeutically effective amount of a compound of formula I in admixture with a pharmaceutically acceptable excipient. Preferred embodiments include the pharmaceutical composition containing the compound of formula I wherein $R_1$, $R_2$, $R_3$, $R_4$, $R_6$, $R_7$ and $R_8$ are identical acyl groups or hydrogen. Particularly preferred are those compounds containing 2 to 8 carbon atoms in each acyl, especially, acyls of the formula —C(=O)-$R_5$, where $R_5$ is lower alkyl as is defined herein.

Additional preferred embodiments include the pharmaceutical compositions including the compound of formula I wherein $R_1$ is one acyl group of the formula —C(=O)-$R_5$ containing 2–8 carbon atoms, particularly lower alkyl; and $R_2$=$R_3$=$R_4$ and $R_6$=$R_7$=$R_8$ are all hydrogen or a different acyl group of the formula —C(=O)-$R_5$ wherein $R_5$ contains 1 to 7 carbon atoms, particularly where $R_5$ is lower alkyl. Preferred compounds include those where $R_1$ is acetyl and $R_2$=$R_3$=$R_4$ where $R_5$ is ethyl, n-propyl n-butyl, i-butyl, t-butyl, n-pentyl, n-hexyl, or n-heptyl and $R_6$, $R_7$ and $R_8$ are hydrogen. Especially preferred compounds are N-acetyl-O,O,O-tri-n-octanoyldeferoxamine and N-acetyl-O,O,O,N,H,H-tetra-n-octanoyldeferoxamine.

An additional embodiment of the present invention describes a method of treating a disease or condition in a human being, related to excess iron in the blood and/or tissue which method comprises administering to a subject in need of such treatment a therapeutically effective amount of the compound of formula I. Preferred embodiments include the method involving the compound of formula I wherein $R_1$, $R_2$, $R_3$, and $R_4$ are identical acyl groups. Particularly preferred are those compounds containing 2 to 8 carbon atoms per acyl, especially, acyls of the formula —C(=O)-$R_5$, where $R_5$ is lower alkyl as is defined herein. Additional preferred embodiments include the pharmaceutical composition including the compound of formula I wherein $R_1$ is one acyl group of the formula —C(=O)-$R_5$ containing 2–8 carbon atoms; and $R_2$=$R_3$=$R_4$=$R_6$=$R_7$=$R_8$ are all hydrogen or a different acyl group from $R_1$ of the formula —C(=O)-$R_5$ wherein $R_5$ contains 1 to 7 carbon atoms, particularly where $R_5$ is lower alkyl. Preferred compounds include those where $R_1$ is acetyl and $R_2$=$R_3$=$R_4$=$R_6$=$R_7$=$R_8$ where $R_5$ is ethyl, n-propyl n-butyl, i-butyl, t-butyl, n-pentyl, n-hexyl or n-heptyl. An especially preferred compound is N-acetyl-O,O,O-tri-n-octanoyldeferoxamine.

Still another embodiment of the present invention describes a process for the preparation of the compounds of formula I which process comprises contacting the unsubstituted deferoxamine wherein $R_1$, $R_2$, $R_3$, $R_4$, $R_6$, $R_7$ and $R_8$ are each hydrogen with a suitable acylating agent in the presence of a strong base having a pK of about 9 to 11, treating the product with a weak base to form the N-acyl-O,O,O-trihydrogendeferoxamine; and treating this material with an excess of one or more different acylating agents to form the compound of formula I. In a preferred embodiment the first suitable acylating agent is $R_5$-C(=O)-X or $R_5$-(C=O)OC(C=O)-$R_5$ where $R_5$ contains 1 to 7 carbon atoms and X is halogen; the weak base has a p$K_b$ value of about 4 to 6; and the second different acylating agent is $R_5$-C(=O)-X or $R_5$(C=O)OC(C=O)$R_5$ wherein $R_5$ contains 1 to 7 carbon atoms and X is halogen. A particularly preferred embodiment is the process wherein $R_5$ of the first acylating agent contains one carbon atom; the weak base is ammonia; and in the different acylating agent $R_5$ contains 4 to 7 carbon atoms. An especially preferred embodiment is the process wherein the first acylating agent is acetyl chloride or acetic anhydride; the base is anhydrous ammonia; and the different acylating agent is octanoyl chloride. The reaction products of formula I may be separated using HPLC or equivalent means.

Process for Preparation

In Reaction Sequence 1, deferoxamine (Ia), as described by M. Windholz, Ed. in *The Merck Index*, published by Merck Co., Inc. of Rahway, N.J. in 1976 (p. 374), is used as a starting material.

REACTION SEQUENCE 1

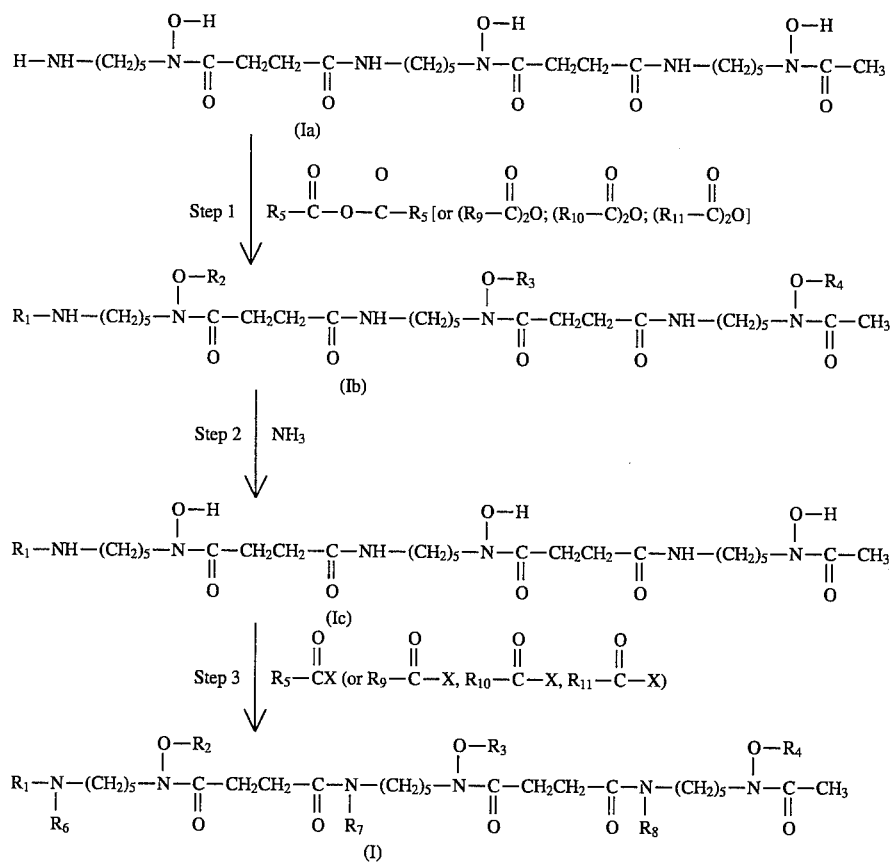

In Step 1, deferoxamine (Ia) is treated with an excess of acyl anhydride, $[R_9(C=O)]_2O$, $[R_{10}(C=O)]_2O$ and $[R_{11}(C=O)]_2O$, in the presence of the alkaline salt of the anhydride in an alcoholic solvent. After about 12 to 24 hours, the solvent and acyl acid are removed under reduced pressure to yield Ib. $R_9$, $R_{10}$ and $R_{11}$ independently may be the same or different groups as is described herein for $R_5$. Thus anhydrides $R_9$-C(=O)-X, $R_{10}$-C(=O)-X and $R_{11}$-C(=O)-X as acyl halides may replace the corresponding anhydride and may be used alone or as a mixture to acylate deferoxamine. If these procedures are used, then it is possible to convert compound of formula Ia to the compound of formula I in one step. [See Example 4 (m) and 6 (m) below.] The reaction product is a mixture which may be used, as a mixture, as a pharmaceutical agent, as is described herein. On the other hand, the products may be separated by methods described herein below and used separately.

Alternatively, deferoxamine (Ia) may be tetra- up to and including hepta-acylated using an acyl halide. Deferoxamine is suspended in a solution of water/solvent (i.e., water/dioxane, about 50/50) and the pH is adjusted to about 9 using a strongly basic solution, preferably 4 to 7N sodium hydroxide. In small portions, the acyl halide in a solvent, such as dioxane, is added dropwise keeping the pH at about 9. Water and a chlorinated solvent, such as chloroform, may be needed to keep the reactants in solution. Strong agitation of the reaction mixture is necessary. The dioxane (and chloroform) phase is removed, washed, dried and removed in vacuo to produce a mixture of compounds of formula Ib and (I). Step 1 and Step 3 below, using acyl halide are often referred to as the Schotten-Baumann reaction, which is described in the art.

In Step 2, the compound of formula Ic is obtained by dissolving the N-acyl-O,O,O-triacyl (to hepta-acyl) product of formula Ib in an excess of an ethereal alcoholic solvent, such as methanol, and cooling to about −20° C. to +20° C., preferably about 0° C., the reaction mixture is subsequently saturated with a base, preferably gaseous ammonia. After maintaining the reaction mixture at about −20° C. to +20° C., preferably at ambient temperature, and allowed to stir for about 24 to 48 hours, the solvent is decanted and the product, usually as a solid, is recovered, washed twice with boiling hexane, and the resulting solid is and dried under reduced pressure. After recrystallization from alcohol/water solution, the product is recovered and air dried.

In Step 3, compound Ic is suspended in a solution of water/solvent (i.e., water/chloroform about 50/50). The solution is adjusted to about pH of 9 using strong base, preferably 3–7N sodium hydroxide solution. To this mixture is added dropwise a solution of the acyl halide, preferably the chloride, in a solvent such as chloroform. The pH of the solution is continuously monitored and is maintained at pH of 9. The layer of chlorinated solvent is removed, washed, dried, filtered, and evaporated in vacuo to produce an oily or waxy product, the compound of formula I.

Isolation and purification of the compounds and intermediates described herein can be effected, if desired, by any suitable separation or purification procedure such as, for example, filtration, extraction, crystallization, column chromatography, high pressure liquid chromatogrophy (HPLC), thin-layer chromatography or thick-layer chromatography, dry column chromatography or a combination of these procedures. Specific illustrations of suitable separation and isolation techniques can be had by reference to the examples herein below. Other equivalent separation or isolation procedures, however, could also be used.

In the preparation of the mixture of compounds of formula I, separation, purification, and identification of the fully acylated or 49 possible partially acylated derivatives of deferoxamine is difficult, uneconomic and sometimes impossible with present separation techniques. Therefore, this invention includes mixtures of compounds of formula I wherein the groups, $R_1$, $R_2$, $R_3$, $R_4$, $R_6$, $R_7$ and $R_8$ are hydrogen or acyl as is defined and as limited above. The mixture of isomers is administered as part of a pharmaceutical composition to a person in the same manner that an essentially pure compound of formula I would be administered.

Although not known with certainty, it appears that of the N-acylated groups $R_6$, $R_7$, and $R_8$, N-$R_6$ is formed first because it is the least sterically hindered of the three available amides. However, it is to be understood that with present analytical techniques, it is not known with certainty which isomer(s) of the derivatives N-$R_6$, N-$R_7$ and N-$R_8$ is present.

PHARMACOLOGY

Several animal models of iron overload have been used to evaluate potential iron-chelating drugs. The hypertransfused rat is one that closely mimics the situation in patients with transfusional iron overload. In this model, heat-damaged rat erythrocytes are transfused intraperitoneally (i.p.) on a daily basis. The iron in the red cells is processed by the reticuloendothelial system, and then transferred to parenchymal cells for storage throughout the body. As expected, the highest concentration of iron is found in the liver and spleen. during drug testing both "new" and "old" iron are available for sequestration and elimination, "new" iron being derived from recently catabolized red cells and "old" iron from parenchymal cells. This is identical to the situation in transfused (iron overload) thalassemia patients.

For 17 years, the hypertransfused rat has been used successfully to screen more than 600 drug candidates. A related model, the hypertransfused mouse, has also been used extensively with some success. In addition, the animal models employing a variety of iron-containing compounds to produce iron overload have been investigated. None of the latter models have proved to be useful in systematically screening a wide variety of iron-chelating agents. In most cases, these models fail to overload the parenchymal and/or reticuloendothelial iron compartments. In vitro models are less useful and correlate poorly with results obtained in vivo, especially following oral drug administration.

All animal models cited have advantages and disadvantages. The hypertransfused rat mode is the most expensive. However, it gives the best prediction that a given compound will cause urinary and/or fecal iron excretion in man.

MATERIALS AND METHODS FOR PHARMACOLOGY

Chelating Agents

Deferoxamine mesylate (DFO:Desferal) was obtained from the Ciba Pharmaceutical Company (Summit, N.J.) as a lyophilized powder. For administration to the hypertransfused rats, it was dissolved in physiological saline at a concentration of 10 mg/ml.

A number of acylated derivatives of DFO were prepared:

$PDP_3$: N-Propionyl-O,O,O-tripropionyl deferoxamine (# of acyl carbons-12), $BDB_3$: N-Butyroyl-O,O,O-tributyryl deferoxamine (# of acyl carbons-16), $VDV_3$: N-Valeroyl-O,O,O-trivaleroyl deferoxamine (# of acyl carbons-20), $MDP_3$: N-Myristoyl-O,O,O-tripropionyl deferoxamine (# of acyl carbons-23).

A homogeneous solution of acylated derivative was obtained by dissolving the drugs in propylene glycol at a concentration of 30 mg/ml.

Animal Model

Sprague-Dawley rats (60–80 g; Taconic Farms, Germantown, N.Y. ( were iron overloaded via daily (5 days/week) intraperitoneal injections of heat-damaged rat erythrocytes. The red blood cells for infusion were purchased from Hilltop Lab Animals, Inc. (Scottsdale, Pa.). They were obtained from retired breeders, the donor animals being exsanguinated via cardiac puncture under $CO_2$ anesthesia. The blood drawn into acid-citrate-dextrose containing gentamicin sulfate (25 g/ml) and shipped on wet ice by overnight express to the testing laboratory. Upon arrival the blood was stored at 4° C. for up to 7 days. Prior to infusion the red cells were slightly damaged by heating at 50° C. for 15 minutes. The recipient animals were infused with the heat-damaged red cells at one-tenth of their blood volume per day for 16 weeks at which time they had received eight blood volumes and were sufficiently iron overload to begin drug screening.

The animals were placed on a low iron diet (>10 μg of Fe/g) for one week prior to screening. Use of a low iron diet is necessary if one is to measure drug related excretion of stool iron. During screening the animals were placed in individual metabolic cages and urine and stool were collected daily. The daily transfusion of heat-damaged red cells was continued throughout drug testing and during intervals of rest between drug evaluations. The compounds were administered either by gavage (orally) or by intraperitoneal injection 4 to 8 hours after the animals were transfused. The dose of each drug was 100 mg/kg/day for 5 days. Urine and stool samples were collected approximately 24 hours after drug administration. They were placed in crucibles, dried at 110° C. and then ashed at 550° C. overnight. Following dissolution of the ash in 3N HCl, the iron content of the samples was determined by atomic absorption spectroscopy.

Screening Protocol

The iron-overloaded rats were divided into groups of six. Before testing any of the new compounds both positive and negative controls were evaluated. Baseline excretion of iron in the urine and stool of this series of hypertransfused rats was determined in the absence of drug administration (negative control). As a positive control, another group of six animals was given DFO intraperitoneally at a dose of 100 mg/kg (153 micromoles/kg). Since the thrust of these studies was to develop an orally-effective drug derived from DFO, a third group of animals was given DFO (100 mg/kg) orally. All of the drugs were evaluated both orally and intraperitoneally. The intraperitoneal effect was used to assess bioavailability.

In the prodrugs, where the hydroxamic acid moieties (iron binding sites) of DFO were blocked, effectiveness upon parenteral administration would indicate that the rat is able to metabolize the prodrug to the active species. Failure to be effective orally could then be attributed to lack of absorption. The standard dose of 100 mg/kg represents the maximum that one can conveniently administer to patients. In order to obtain an estimate of the relative iron-chelating potency within the series, the amount of iron excreted in response to the acylated derivatives was normalized to correspond to the molar equivalent of 100 mg/kg DFO.

Results and Discussion for Rat Testing

Table 1 outlines the protocol followed for prodrug evaluation.

Table 2 gives the background iron excretion of the model, as well as that induced by oral and parenteral DFO.

For comparison, historical DFO drug data are also given, Grady, R. W., et al., *Journal of Pharmacol, Exp. Therap.*, Vol. 209, p. 342–348 (1979). Oral administration of DFO is usually less than 10% as effective as parenteral administration. While rigorous conclusions should not be made on the basis of a single evaluation, it can be said with some certainty that the hypertransfused rat model gives reasonable indication of relative efficacy; it has never failed to reveal a potentially useful compound.

A critical evaluation of the historical data indicates there is no correlation between the overall amount of blood transfused and the amount of iron excreted in response to DFO. Thus, once a significant iron overload has been established, its relative magnitude does not appear to determine the amount of iron excreted in response to a give drug. This is to be expected since the accessibility of the chelatable pools and the rate at which they refilled are considered greater factors in this regard. Because "new" iron, that derived from catabolism of recently transfused erythrocytes, probably accounts for a significant portion of the iron excreted, the interval between trans- fusion and drug administration and the degree to which the transfused red cells were heat damaged prior to infusion undoubtedly contributes to the variability of the results.

The results of screening the acylated DFO derivatives are presented in Tables 3 and 4. When differences in molecular weight are taken into account, three of the derivatives caused about 1.5 and 2.0 times greater net iron excretion than DFO when given parenterally.

These results suggest that the protecting groups are slowly cleaved by esterases within the body, resulting in a prolonged release of active drug. These results further suggest that the relative efficacy of cleavage increases as the length of the acyl groups increases, up to a maximum of about five carbons. The shift toward increased urinary

TABLE 1

Screening Schedule in the Hypertransfused Rat Model of Iron Overload

| Compound | Route | Dose mg/kg |
| --- | --- | --- |
| Control | — | |
| DFO | ip/po | 100 |
| $VDV_3$ | ip/po | 100 |
| $PDP_3$ | ip/po | 100 |
| $BDB_3$ | ip/po | 100 |
| $MDP_3$ | ip/po | 100 |

TABLE 2

Iron Excreted by Hypertransfused Rats In the Presence and Absence of Deferoxamine

| | | | | GROSS | | NET | |
| --- | --- | --- | --- | --- | --- | --- | --- |
| Compound | Dose (mg/kg) | Route | n | Urine (µg/kg/day) | Stool (µg/kg/day) | Urine (µg/kg/day) | Stool (µg/kg/day) |
| A Background | | | 6 | 93 | 392 | | |
| B DFO | 100 | ip | 54 | 180 | 857 | 87 | 465 |
| | 100 | po | 6 | 98 | 398 | 5 | 6 |

A = Non-treated background control
B = DFO (historic)

TABLE 3

Iron Excreted by Hypertransfused Rats in Response to Deferoxamine Derivatives (Intraperitoneally)

| | Dose | | GROSS | | NET | | | | |
| --- | --- | --- | --- | --- | --- | --- | --- | --- | --- |
| | | | Urine | Stool | Urine | Stool | Urine | Stool | TOTAL |
| Compound | mg/kg | µmoles/kg | µg/kg/day | | µg/kg/day/µmole | | µg/kg/day/µmole | | µg/kg/day/µmole |
| Background | | | 93 | 392 | 0.51 | 2.18 | | | |
| DFO | 100 | 153 | 180 | 857 | 1.18 | 5.60 | 0.67 | 3.42 | 4.09 |
| $PDP_3$ | 100 | 128 | 179 | 933 | 1.40 | 7.29 | 0.89 | 5.11 | 6.00 |
| $BDB_3$ | 100 | 119 | 174 | 875 | 1.46 | 7.35 | 0.95 | 5.17 | 6.12 |
| $VDV_3$ | 100 | 112 | 184 | 966 | 1.64 | 8.63 | 1.13 | 6.45 | 7.58 |
| $MDP_3$ | 100 | 107 | 134 | 434 | 1.25 | 4.06 | 0.74 | 1.88 | 2.62 |

$PDP_3$ = N-propionoyl-O,O,O-tripropionoyldeferoxamine
$BDB_3$ = N-butyroyl-O,O,O-tributyroyldeferoxamine
$VDV_3$ = H-valeroyl-O,O,O-trivaleroyldeferoxamine
$MDP_3$ = N-myristoyl-O,O,O-tripropionoyldeferoxamine

TABLE 4

Iron Excreted by Hypertransfused Rats in Response to Deferoxamine Derivatives (Orally)

| Compound | Dose mg/kg | Dose μmoles/kg | GROSS Urine μg/kg/day | GROSS Stool μg/kg/day | GROSS Urine μg/kg/day/μmole | GROSS Stool μg/kg/day/μmole | NET Urine μg/kg/day/μmole | NET Stool μg/kg/day/μmole | TOTAL μg/kg/day/μmole |
|---|---|---|---|---|---|---|---|---|---|
| Background | | | 93 | 392 | 0.51 | 2.18 | | | |
| DFO | 100 | 153 | 98 | 398 | 0.64 | 2.60 | 0.03 | 0.03 | 0.06 |
| PDP$_3$ | 100 | 128 | 99 | 496 | 0.77 | 3.88 | 0.26 | 1.70 | 1.96 |
| BDB$_3$ | 100 | 119 | 91 | 507 | 0.76 | 4.26 | 0.25 | 2.08 | 2.33 |
| VDV$_3$ | 100 | 112 | 133 | 599 | 1.19 | 5.35 | 0.68 | 3.17 | 3.85 |
| MDP$_3$ | 100 | 107 | 88 | 551 | 0.82 | 5.15 | 0.31 | 2.97 | 3.28 |

PDP$_3$ = N-propionoyl-O,O,O-tripropionoyldeferoxamine
BDB$_3$ = N-butyroyl-O,O,O-tributyroyldeferoxamine
VDV$_3$ = H-valeroyl-O,O,O-trivaleroyldeferoxamine
MDP$_3$ = N-myristoyl-O,O,O-tripropionoyldeferoxamine iron excretion in response to intraperitoneally injected PDP$_3$, BDB$_3$ and VDV$_3$, suggests that these compounds circulate for a longer period of time than DFO and are thus able to chelate more "new" iron coming from the reticuloendothelial cells.

Inspection of Table 4 shows that, upon oral administration of the acylated DFO derivatives, promising results were obtained, especially when the results were normalized for dosage. (In order to compare the relative efficacy of members of a homologous series, it is necessary to administer equivalent molar quantities of each drug, rather than identical weights). The net iron excretion induced by oral PDP$_3$, BDB$_3$ and VDV$_3$, indicates that these compounds were efficiently absorbed and subsequently cleaved. Oral VDV$_3$, in fact, caused more than 60 times more iron to be excreted than DFO given orally.

The net total iron excretions produced by i.p. administration of PDP$_3$, BDB$_3$ and VDV$_3$ exceeded that for i.p. deferoxamine by 50% to 100% (Table 3 and FIG. 1). The corresponding data for the orally administered prodrugs exceeded the iron excretion rate of oral DFO by factors of 30 to 60 (Table 4 and FIG. 2). As expected, the efficacy increased as the length of the acyl group increased (due in part to the greater lipophilicity of the derivatives). This effect is particularly evident after oral administration of the two drugs with the same size O-acyl groups, PDP$_3$ and MDP$_3$. Increasing the lipophilic loading on the nitrogen atoms in the deferoxamine chain by lengthening the N-terminal amide from 3 carbons to 14 carbons increases the potency (absorption) by two-thirds. The maximum rate of hydrolysis of the esters (activation) was predicted to occur with chain length of four to six carbon atoms (butyl to caproyl). Therefore, the valeryl group (5 carbons) appears to be near the optimum size for an acyl protecting group). In addition, from earlier unpublished data, it is clear that increasing the number of N-acyl groups is highly effective in increasing oral efficacy; thus, adding an N-acyl group on the N-terminal amide, e.g. going from N-acetyl-O,O,O-trioctanoyldeferoxamine to N-acetyl-N-octanoyl-O,O,O-trioctanoyldeferoxamine increases absorption about 50%. The most significant aspect of the present study is that all of the acyl prodrugs, when administered orally, are at least half as active as intraperitoneal deferoxamine on a molar basis.

The most effective oral drug studied, VDV$_3$, induces a total iron excretion of 3.85 μg/kg/day/umole, which is 94% of the historically observed excretion induced by intraperitoneal deferoxamine, 4.09 μg/kg/day/umole.

The value of VDV$_3$ is further enhanced by its lack of systemic toxicity. The intraperitoneal LD$_{50}$s of both DFO and VDV$_3$ were 800 mg/kg in Swiss-Webster mice.

These results and earlier results indicate that:

(1) Hydrolysis of the O-acyl groups of these DFO derivatives occurs in rats after intraperitoneal and oral administration.

(2) Gastrointestinal absorption is enhanced by both N- and O-acylation.

(3) VDV$_3$ has the most active derivative tested.

(4) Oral VDV$_3$ has about 94% of the chronic iron excretory potency of i.p. DFO.

(5) Increasing the length of the N-acyl group (while keeping the 0-acyl group constant) increases the potency of the derivatives.

(6) Increasing the number of N-acyl groups increases the potency of the compounds.

(7) These prodrugs have a depot effect when administered i.p.

In one embodiment, the present invention relates to a pharmaceutical composition for oral administration to a mammal to mitigate metal ion overload conditions of the structure:

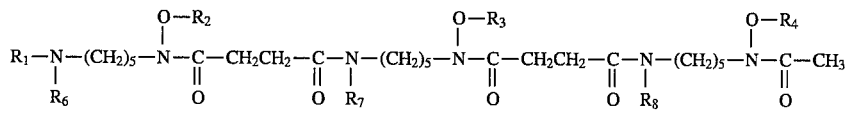

(1A)

wherein R$_6$, R$_7$ and R$_8$ are each —H, and

R$_1$ is selected from —(C=O)-R$_5$ wherein is selected from alkyl groups having from 3 to 6 carbon atoms, R$_2$, R$_3$ and R$_4$ are each independently selected from acyl group —(C=O)-$_{5a}$ where R$_{5a}$ is selected from alkyl groups having from 3 to 6 carbon atoms, and the total number of carbon atoms in groups R$_1$, R$_2$, R$_3$ and R$_4$ is between 12 and 28.

In another embodiment, the pharmaceutical composition has R$_1$, R$_2$, R$_3$ and R$_4$ each selected from identical alkyl groups.

Another embodiment is the pharmaceutical composition wherein in groups R$_5$ and R$_{5a}$ the alkyl group has 2 carbon atoms, ethyl.

Another embodiment is the pharmaceutical composition wherein in groups $R_5$ and $R_{5a}$ the alkyl group has 3 carbon atoms, n-propyl or isopropyl.

Another embodiment is the pharmaceutical composition wherein in groups $R_5$ and $R_{5a}$ the alkyl group has 4 carbon atoms, n-butyl, isobutyl sec-butyl or tert-butyl.

Another embodiment is the pharmaceutical composition wherein in groups $R_5$ and $R_{5a}$ the alkyl group has 5 carbon atoms, n-pentyl or isopentyl.

Another embodiment is the pharmaceutical composition wherein in groups $R_5$ and $R_{5a}$ the alkyl group has 6 carbon atoms, n-hexyl and isohexyl.

Another embodiment is the pharmaceutical composition wherein the ion is selected from iron$^{+3}$ or aluminum$^{+3}$.

In another embodiment, the pharmaceutical composition of the structure:

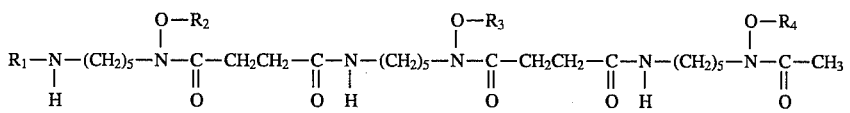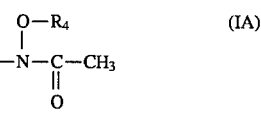

has $R_1$ as myristoyl (the tetradecanoic acid ester) and $R_2$, $R_3$ and $R_4$ are each acyl groups wherein the acyl group is propionyl.

The acyl halides and anhydrides, solvents, reagents and the like described herein are available according to *Chemical Sources*, published by Directories Publishing Company, Inc., Flemington, N.J. in 1979. Those halides or anhydrides not available are prepared according to methods known or adapted from the art, see for example, R. Morrison and R. Boyd, *Organic Chemistry*, 3rd ed., published by the Benjamin Co. in 1976.

Utility And Administration

Administration of the compounds of this invention can be via any of the accepted modes of administration for therapeutic agents. These methods include oral, parenteral, transdermal, subcutaneous and other systemic modes. The preferred method of administration is oral.

Depending on the intended mode, the composition may be in many forms, for example, solid, semisolid, or liquid dosage forms, including tablets, time release agents, pills, capsules, suspensions, solutions and the like. The compositions will include a conventional pharmaceutical excipient and an active compound of formula I or the pharmaceutically acceptable salts thereof and may, in addition, include other medicinal agents, pharmaceutical agents, carriers, adjuvants, diluents, etc.

The amount of the active compound of formula I administered will, of course, be dependent on the molecular weight of selected compound, the subject being treated, the subject's weight, the severity of the affliction, the manner of the administration and the judgment of the prescribing physician. However, an effective dose is in the range of about 25–200 mg/kg/day, preferably about 125 mg/kg/day. For an average 70 kg human, those dosages would amount to about 1.5 to 14 g/day, or preferably about 9 g/day.

For solid compositions, conventional nontoxic solids include for example, pharmaceutical grades of mannitol, lactose, starch, magnesium stearate, cellulose and the like may be used. Liquid pharmaceutically administratable compositions can be prepared by dissolving, dispersing, etc., a compound of formula I and optional pharmaceutical adjuvants in an excipient, such as, for example, water, glycerol, ethanol, vegetable oil and the like to form a suspension. Actual methods of preparing such dosage forms are known, or will be apparent to those skilled in the art; see, for example, *Remington's Pharmaceutical Sciences*, Mack Publishing Company, Easton, Pa., 15th Edition, 1975.

The following preparations and examples serve to illustrate the invention. They should not be construed as narrowing it, nor as limiting its scope.

EXAMPLE 1

Preparation of N-Acetyl O,O,O-triacetyldeferoxamine (a) Deferoxamine mesylate (13.1 g) and 1.66 g of anhydrous sodium acetate are dissolved in 200 ml of methanol. The methanol solution is boiled to complete the solution. The reaction mixture is then rapidly cooled to ambient temperature and treated immediately (before crystallization starts) with 180 ml of acetic anhydride. The mixture is maintained overnight (about 16 hrs) in the absence of moisture and then concentrated under vacuum to produce an oily residue. This residue is freed from acetic acid by evaporation under vacuum using two portions of 200 ml of butanol. The oily residue is air dried for several days to produce 14.1 g of crude N-acetyl-O,O,O-triacetyldeferoxamine. The proton magnetic resonance spectrum of the recrystallized product is consistent with this structure; [structural unit, parts per million (ppm) downfield from tetramethysilane (TMS) reference]:

(for C-H absorption):

-N-C-C-CH$_2$-C-C-N-O-: 1.44;

-N-C-C-C-CH$_2$-C-N-O-: 1.52;

-N-C-CH2-C-C-C-N-O-: 1.58;

CH$_3$-C(=O)-N-(OCO-C-); 1.95;

CH$_3$-C(=O)-NH-C-C-C-; 1.99

-C-C(=O)-N-(O-CO-CH$_3$); 2.17;

-N-C(=O)-CH$_2$-CH$_2$-(C=O)-N-; 2.56;

-C-C-CH$_2$-N(-O)-(C=O)-; 3.22;

-C-(C=O)-NH-CH2-C-; 3.70; and (for the N-H absorption):

-C-C(=O)-NH-C-C-; 6.28.

(b) Similarily proceeding as in Subpart (a) above but substituting a stoichiometrically equivalent amount of propionyl anhydride;

butyryl anhydride;

valeryl anhydride:

isovaleryl anhydride;

octanoyl anhydride;

dodecanoyl anhydride;

palmitoyl anhydride;

stearoyl anhydride; or hexacosanoyl anhydride instead of acetic anhydride, there is obtained the corresponding N-propionyl-O,O,O-tripropionyldeferoxamine;

N-butyryl-O,O,O-tributyryldeferoxamine;

N-valeryl-O,O,O-trivaleryldeferoxamine;

N-isovaleryl-O,O,O-triisovaleryldeferoxamine;

N-octanoyl-O,O,O-trioctanoyldeferoxamine;

N-dodecanoyl-O,O,O-tridodecanoyldeferoxamine;

N-palmitoyl-O,O,O-tripalmitoyldeferoxamine;

N-stearoyl-O,O,O-tristearoyldeferoxamine; or

N-hexacosanoyl-O,O,O-tri(hexacosanoyl)deferoxamine.

It is often necessary to employ larger volumes of solvents to keep the substituted deferoxamine in solution and to obtain more complete acylation of the three hydroxamic acids.

(c) Similarily, when proceeding as in Subpart (a) above but substituting less than a stoichiometrically equivalent amount of the acyl anhydride, there is obtained a compound wherein the N-acyl group is formed and a mixture containing less than complete acylation of the hydroxamic acid groups of deferoxamine. Such mixtures when acetic anhydride is used include the following compounds:

N-acetyl-O,O,O-hydrogendiacetyldeferoxamine and

N-acetyl-O,O,O-dihydrogenacetyldeferoxamine.

The exact positions of the acetyl and hydrogen groups on the hydroxamines is not yet established.

(d) Similarily proceeding as in Subpart (a) above but substituting a stoichiometrically equivalent amount of a mixture of the following anhydrides:

acetic anhydride, propionic anhydride, and burytic anhydride; or acryloyl anhydride, acetic anhydride, propionic anhydride, and burytic anhydride instead of acetic anhydride, there is obtained a mixture of corresponding tetraacyl derivatives including:

N-acetyl-O,O,O-acetylpropionylbutyryldeferoxamine;

N-butyryl-O,O,O-acetylpropionylbutyryldeferoxamine; and

N-propionyl-O,O,O-butyrylpropionylacetyldeferoxamine: or

N-acryloyl-O,O,O-acetylpropionylbutyryldeferoxamine;

N-acetyl-O,O,O-butyrylpropionylacryloyldeferoxamine; and

N-butyryl-O,O,O-acryloylpropionylacetyldeferoxamine

The exact positions of the acyl groups on the hydroxamines is not yet established with certainty.

EXAMPLE 2

Preparation of N-Acetyl-O,O,O-trihydrogendeferoxamine (a) N-Acetyl-O,O,O-triacetyldeferoxamine (prepared in Example 1) (10.0 g) is taken up in 200 ml of methanol and 500 ml of ether, cooled to 0° C., and the solution is saturated with anhydrous gaseous ammonia. The reaction mixture is kept at 0° C. for 6 hr, and then at ambient temperature overnight (about 16 hr). The ammonia-containing methanol/ether is decanted and the resulting colorless crystalline solid is washed twice with boiling hexane and is dried in vacuum, crude yield 8.1 g. After two recrystallizations using methanol/water ( 60/40 ), there are obtained about 7.0 grams of N-acetyl-O,O,O-trihydrogendeferoxamine, m.p. 179°–181° . The infrared spectrum and proton magnetic resonance spectrum are consistent with the structure.

(b) Similarily, proceeding as in Subpart (a) of this Example, but substituting a stoichiometrically equivalent amount of:

N-propionyl-O,O,O-tripropionyldeferoxamine;

N-butyryl-O,O,O-tributyryldeferoxamine;

N-valeryl-O,O,O-trivaleryldeferoxamine;

N-octanoyl-O,O,O-trioctanoyldeferoxamine;

N-palmitoyl-O,O,O,-tripalmitoyldeferoxamine; or

N-pentacosanoyl-O,O,O-tripentacosanoyldeferoxamine instead of the N-acetyl-O,O,O-triacetyldeferoxamine, there is obtained the corresponding N-propionyl-O,O,O-trihydrogendeferoxamine;

N-butyryl-O,O,O-trihydrogendeferoxamine;

N-valeryl-O,O,O-trihydrogendeferoxamine;

N-octanoyl-O,O,O-trihydrogendeferoxamine;

N-palmitoyl-O,O,O-trihydrogendeferoxamine; or

N-pentacosanoyl-O,O,O-trihydrogendeferoxamine.

EXAMPLE 3

Preparation of N-Acetyl-O,O,O-tripalmitoyldeferoxamine (a) N-Acetyl-O,O,O-trihydrogendeferoxamine (from Example 2) (6.0 g) is suspended in a solution of ml of water end 50 ml of dioxane. The well-agitated suspension is adjusted to pH of 9 using 5N sodium hydroxide solution. To this mixture is added in 10 ml portions, a solution of 16.5 g of palmitoyl chloride in 60 ml of dioxane. The pH of 9 of the mixture is maintained by the addition of a 5N sodium hydroxide solution after each 10 ml portion of the acyl chloride solution. After 40 ml of the palmitoyl chloride solution are added, 50 ml of water and 200 ml of chloroform are added to facilitate the mixing of the solution. After the addition of the palmitoyl chloride solution is completed, the reaction mixture is stirred for 1 hr, with periodic monitoring to maintain a pH of 9. The reaction mixture is then diluted with 150 ml of water and 500 ml of chloroform, and centrifuged to separate the phases. The white material present at the liquid interface is discarded. [The aqueous phase is separated and extracted twice with 250 ml of chloroform. Essentially no product is obtained upon removal of the chloroform.] The chloroform phase contained a white solid which is removed using additional centrifugation. The combined chloroform layers are washed twice with saturated sodium bicarbonate solution, twice with saturated sodium chloride solution, dried over anhydrous sodium sulfate, filtered and evaporated using reduced pressure. About 14 g of a crude, creamy white waxy solid is obtained which is highly soluble in chloroform. The waxy solid was triturated twice with 100 ml of ether to remove the palmitic acid formed. The insoluble residue, 11.8 g, was recrystallized from methanol/ethanol (3/1). The solid is air dried to produce 6.1 g of solid N-acetyl-O,O,O-tripalmitoyldeferoxamine. The nuclear magnetic resonance spectrum is consistent with the structure.

EXAMPLE 3A

Preparation of N-Acetyl-O,O,O,-N,H,H-tetraoctanoyldeferoxamine (a) N-Acetyl-O,O,O-trihydrogendeferoxamine (from Example 2) (3.0 g) is suspended in a mixture of 100 ml of water and 150 ml of chloroform. The suspension is adjusted to pH 9 using 5N sodium hydroxide. To the well-agitated mixture is added dropwise, over a period of 45 min, a solution of 7.3 g octanoyl chloride in 50 ml of chloroform. The mixture is continuously maintained at pH 9 by the addition of 5N sodium hydroxide as necessary. After the addition of the octanoyl chloride is completed, the reaction mixture is stirred for 1 hr, with periodic monitoring to maintain a pH of 9. The chloroform phase is removed and the aqueous phase is extracted two times with 100 ml of chloroform, centrifuging to break the emulsion when necessary. The combined chloroform layers are washed twice with saturated sodium bicarbonate solution, twice with saturated sodium chloride solution, dried over anhydrous sodium sulfate, filtered and evaporated under reduced pressure. The syrupy residue is triturated twice with 50 ml of ether to remove the octanoic acid formed. The insoluble residue (2.6 g) is dissolved in dichloromethane and fractionated by HPLC.

Four main fractions are obtained at the following retention times: 2.4 min (11% relative abundance), 3.4 min (29%), 4.7 min (15%) and 7.0 min (40%) using a 5 micron silica-CN column and a methanol gradient from 2% to 5% over 12 min in a mixture containing 25% chlorobutane and iso-octane at a flow rate of 2 ml/min.

Fraction number 3 (4.7 min) (amounting to mg) was determined by 300 MHz NMR to be N-acetyl-O,O,O-tetraoctanoyl-N-octanoyldeferoxamine. Fraction number 4 (7.0 min) (amounting to 799 mg) was determined by 300 MHz NMR to be N-acetyl-O,O,O-trioctanoyldeferoxamine. The 300 MHz proton nuclear magnetic resonance (NMR) spectral results are shown below in Table III.

and the waxy residue is dissolved in 500 ml of diethyl ether and hexane was added almost to turbidity. A sticky, granular product weighing 3.8 g is obtained. The infrared and proton magnetic resonance spectra are consistent with a structure of N-octanoyl-O,O,O-trioctanoyldeferoxamine.

(b) Similarily, proceeding as in Subpart (a) above, but substituting a stoichiometrically equivalent amount of acetyl chloride;

propionyl chloride;

butyryl chloride;

pivalyl chloride;

valeryl chloride;

isovaleryl chloride;

dodecanoyl chloride;

palmitoyl chloride; or hexacosanoyl chloride instead of octanoyl chloride, there is obtained the corresponding N-acetyl-O,O,O-triacetyldeferoxamine;

N-propionyl-O,O,O-tripropionyldeferoxamine;

TABLE III

Proton NMR Results

| CHEMICAL SHIFT | Assignment | Fract. 3 Actual | Fract. 3 Theory | Fract. 4 Actual | Fract. 4 Theory |
|---|---|---|---|---|---|
| 0.9 | $C\underline{H}_3$—$(CH_2)_5$— | 12. | 12. | 9. | 9. |
| 1.4 | $CH_3(C\underline{H}_2)_5CH_2$— | 62. | 58. | 54. | 48. |
| 1.8 | —$NCH_2(C\underline{H}_2)_3CH_2N$— | | | | |
| 2.0 | $C\underline{H}_3$—(C=O)—N— | | | | |
| 2.1 | —O—N—(C=O)—$C\underline{H}_3$ | 5.5 | 6. | 6.2 | 6. |
| 2.7 | (O=C)$C\underline{H}_2C\underline{H}_2$(C=O) | 15.5 | 16. | 15.4 | 14. |
| | N—O—(C=O)—$C\underline{H}_2$— | | | | |
| 3.3 | O—N—$C\underline{H}_2$—C | 4.6 | 6. | 6.9 | 6. |
| 3.7 | (O=C)—N—$C\underline{H}_2$—C | 9. | 6. | 7.7 | 6. |
| | (proton total) | 108.6 | 106. | 99.2 | 92. | a - ppm from tetramethylsilane (TMS) as reference.
(b) Similarly, proceeding as is described in Subpart
(a) above of this Example using BW separation there is obtained: N-acetyl-O,O,O,N,H,N-pentaoctanoyl deferoxmine; and N-acetyl-O,O,O,N,N,N-hexaoctanoyl deferoxamine.

EXAMPLE 4

Preparation of N-Octanoyl-O,O,O-trioctanoyldeferoxamine (Step 1, Schotten-Baumann conditions)

(a) Deferoxamine mesylate (6.0g) is suspended in 50 ml of water and 50 ml of dioxane. The suspension is adjusted to pH of 9 using 5N sodium hydroxide solution with strong agitation. In 10 ml portions, a solution of 13.0 g of octanoyl chloride in 60 ml of dioxane. The pH of the mixture is maintained at 9 by the dropwise addition of the 5N sodium hydroxide solution. After the addition of 40 ml of the octanoyl chloride/dioxane solution, the reaction mixture is treated with 50 ml of water and 200 ml of chloroform. The mixture separates into two phases which are agitated strongly. After the addition of all the acid chloride solution, the reaction mixture is agitated for 2 hr at pH of 9. The reaction mixture is diluted with 500 ml of water and 1000 ml of chloroform and the aqueous phase is separated and extracted twice using 250 ml portions of chloroform. The combined chloroform phases are washed twice with saturated sodium bicarbonate solution, twice with saturated sodium chloride solution and dried using anhydrous sodium sulfate. The chloroform is removed under reduced pressure, N-butyryl-O,O,O-tributyryldeferoxamine;

N-pivalyl-O,O,O-tripivalyldeferoxamine;

N-valeryl-O,O,O-trivaleryldeferoxamine;

N-isovaleryl-O,O,O-triisovaleryldeferoxamine;

N-dodecanoyl-O,O,O-tridodecanoyldeferoxamine;

N-palmitoyl-O,O,O-tripalmitoyldeferoxamine; or

N-hexacosanoyl-O,O,O-trihexacosanoyldeferoxamine.

(c) Similarily, proceeding as in Subpart (a) above, but substituting a stoichiometrically equivalent amount of 3-chlorobutanoyl chloride;

3-chloroisovaleryl chloride;

10-chlorooctadecanoyl chloride;

10-methoxyoctadecanoyl chloride;

9,10-dichlorooctadecanoyl chloride;

9,10-dibromooctadecanoyl chloride; or 9,10-dimethoxyoctadecanoyl chloride;

instead of octanoyl chloride, there is obtained the corresponding

N-(3-chlorobutanoyl)-O,O,O-tri(3-chlorobutanoyl)deferoxamine;

N-(3-chloroisovaleryl)-O,O,O-tri(3-chloroisovaleryl)deferoxamine;

N-(10-chlorooctadecanoyl)-O,O,O-tri(10chlorooctadecanoyl)deferoxamine;

N-(10-methoxyoctadecanoyl)-O,O,O-tri(10-methoxyoctadecanoyl)deferoxamine;

N-(9,10-dichlorooctadecanoyl)-O,O,O-tri(9,10-dichlorooctadecanoyl)deferoxamine;

N-(9,10-dibromooctadecanoyl)-O,O,O-tri(9,10-dibromooctadecanoyl)deferoxamine; or N-(9,10-dimethoxyoctadecanoyl)-O,O,O-tri(9,10-dimethoxyoctadecanoyl)deferoxamine.

(d) Similarly proceeding as in Subpart (a) above, but substituting a stoichiometrically equivalent amount of acryloyl chloride:

2-butenoyl chloride;

2-pentenoyl chloride;

2-octenoyl chloride;

oleoyl chloride; or 2-pentacosenoyl chloride instead of octanoyl chloride, there is obtained the corresponding N-acryloyl-O,O,O-triacryloyldeferoxamine;

N-2-butenoyl-O,O,O-tri(2-butenoyl)deferoxamine;

N-2-pentenoyl-O,O,O-tri(2-pentenoyl)deferoxamine;

N-2-octenoyl-O,O,O-tri(2-octenoyl)deferoxamine;

N-2-oleoyl-O,O,O-trioleoyldeferoxamine; or

N-2-pentacosenoyl-O,O,O-tri(2-pentacosenoyl)deferoxamine.

(e) Similarly proceeding as in Subpart (a) above, but substituting a stoichiometrically equivalent amount of 2-chloroacryloyl chloride;

2-chloropropenoyl chloride;

4-methoxybutenoyl chloride;

2-chlorooctenoyl chloride;

2-chlorooleoyl chloride; or 2-chloropentacosenoyl chloride.

instead of octanoyl chloride, there is obtained the corresponding

N-2-chloroacryloyl-O,O,O-tri(2-chloroacryloyl)deferoxamine;

N-(2-chloropropenoyl)-O,O,O-tri(2-chloropropenoyl)deferoxamine;

N-(4-methoxybutenoyl)-O,O,O-tri(4-methoxybutenoyl)deferoxamine;

N-(2-chlorooctenoyl)-O,O,O-tri(2-chlorooctenoyl)deferoxamine; or

N-(2-chloropentacosenoyl)-O,O,O-tri(2-chloropentacosenoyl)deferoxamine.

(f) Similarly proceeding as in Subpart (a) above, but substituting a stoichiometrically equivalent amount of cyclopropylacetyl chloride;

cyclobutylacetyl chloride;

cyclohexylpropanoyl chloride;

cyclodecyldecanoyl chloride; or cyclopentacosanylacetyl chloride instead of octanoyl chloride, there is obtained the corresponding N-cyclopropylacetyl-O,O,O-tri(cyclopropylacetyl)deferoxamine;

N-cyclobutylacetyl-O,O,O-tri(cyclobutylacetyl)deferoxamine;

N-cyclohexylpropanoyl-O,O,O-tri(cyclohexylpropanoyl) deferoxamine;

N-cyclodecyldecanoyl-O,O,O-tri(cyclodecyldecanoyl) deferoxamine; or

N-cyclopentacosanylacetyl-O,O,O-tri(cyclopentacosanylacetyl)deferoxamine.

(g) Similarily proceeding as in Subpart (a) above, but substituting a stoichiometrically equivalent amount of 2-chlorocyclopropylacetyl chloride 4-chlorocyclohexylacetyl chloride 2-chlorocyclopentadecylacetyl chloride;

or 10-(2-chloropentacosanyldecanoyl chloride instead of octanoyl chloride, there is obtained the corresponding N-(2-chlorocyclopropylacetyl)-O,O,O-tri(2-chlorocyclopropylacetyl)deferoxamine;

N-(4-chlorocyclohexylacetyl)-O,O,O-tri(4-chlorocyclohexylacetyl)deferoxamine;

N-(2-chlorocyclopentadecylacetyl)-O,O,O-tri(2-chlorocyclopentadecylacetyl)deferoxamine; or N-[10-(2-chloropentacosanyl)decanoyl]-O,O,O-tri[10-(2-chloropentacosanyl)decanoyl]deferoxamine.

(h) Similarily proceeding as in Subpart (a) above, but substituting a stoichiometrically equivalent amount of propynoyl chloride;

2-hexynoyl chloride;

2-decynoyl chloride; or 2-pentacosynoyl chloride instead of octanoyl chloride, there is obtained the corresponding N-(propynoyl)-O,O,O-tri(propynoyl)deferoxamine;

(2-hexynoyl)-O,O,O-tri(2-hexynoyldeferoxamine;

N-(2-decynoyl)-O,O,O-tri(2-decynoyl)deferoxamine; or

N-(2-pentacosynoyl)-O,O,O-tri(2-pentacosynoyl)deferoxamine.

(i) Similarily proceeding as in Subpart (a) above, but substituting a stoichiometrically equivalent amount of 4-chloro-2-butynoyl chloride;

10-chloro-2-decynoyl chloride;

15-chloro-3-pentadecynoyl chloride; or 25-chloro-2-pentacosynoyl chloride instead of octanoyl chloride, there is obtained the corresponding N-(4-chloro-2-butynoyl)-O,O,O-tri(4-chlorobutynoyl)deferoxamine;

N-(10-chloro-2-decynoyl)-O,O,O-tri(10-chloro-2-decynoyl)deferoxamine;

N-(15-chloro-3-pentadecynoyl)-O,O,O-tri(15-chloro-3-pentadecynoyl)deferoxamine; or N-(25-chloro-2-pentacosynoyl)-O,O,O-tri(25-chloro-2-pentacosynoyl)deferoxamine.

(j) Similarily proceeding as in Subpart (a) above, but substituting a stoichiometrically equivalent amount of benzoyl chloride:

2-naphthoyl chloride; or 1-phenanthroyl chloride for octanoyl chloride, there is obtained the corresponding N-benzoyl-O,O,O-tri(benzoyl)deferoxamine;

N-(2-naphthoyl)-O,O,O-tri(2-naphthoyl)deferoxamine; or

N-(1-phenanthroyl)-O,O,O-tri(1-phenanthroyl)deferoxamine.

(k) Similarly proceeding as in Subpart (a) above, but substituting a stoichiometrically equivalent amount of 4-chlorobenzoyl chloride:

6-methoxy-2-naphthoyl chloride; or 6-chloro-l-phenanthroyl chloride instead of octanoyl chloride, there is obtained the corresponding N-(4-chlorobenzoyl)-O,O,O-tri(4-chlorobenzoyl)deferoxamine;

N-(6-methoxy-2-naphthoyl)-O,O,O-tri(6-methoxy-2-naphthoyl)deferoxamine; or

N-(6-chloro-1-phenanthroyl)-O,O,O-tri(6-chloro-1-phenanthroyl)deferoxamine.

(l) Similarly, proceeding as in Subpart (a) above but substituting a stoichiometrically equivalent amount of phenylacetyl chloride;

10-phenyldecanoyl chloride; or 2-naphthyldecanoyl chloride; instead of octanoyl chloride, there is obtained the corresponding N-(phenylacetyl)-O,O,O-tri(phenylacetyl) deferoxamine;

N-(10-phenyldecanoyl)-O,O,O-tri(10 -phenyldecanoyl) deferoxamine; or

N-(2-naphthyldecanoyl)-O,O,O-tri(2-naphthyldecanoyl) deferoxamine.

(m) Similarily, proceeding as is described in Subpart (a) of this Example, but substituting a stoichiometrically equivalent amount of the following equimolar mixtures of acyl chlorides:

A. acryloyl chloride, butyryl chloride, benzoyl chloride, and cyclohexyl carbonyl chloride;

B. 2-naphthoyl chloride, 2-butynoyl chloride, phenylacetyl chloride, and 4-chlorophenylacetyl chloride; or C. 3-chloropropionyl chloride, 4-chloro-2-butenoylchloride, 4-chlorocyclohexylcarbonyl chloride, and 4-chlorocyclohexylacetyl chloride for butyryl chloride.

there is obtained the following mixtures of tetraacyldeferoxamines:

A. N-acryloyl-O,O,O-butyrylbenzoylcyclohexyldeferoxamine; N-cyclohexyl-O,O,O-benzoylacryloylbutyryldeferoxamine; and N-benzoyl-O,O,O-butyrylacryloylcyclohexylcarbonyl deferoxamine.

B. N-(2-naphthoyl )-O,O,O-butynoylphenylacetyl-4-chlorophenylacetyldeferoxamnine; N-phenylacetyl-O,O,O-butynoyl-4-chlorophenylacetyl-(2-naphthoyl)deferoxamine; and N-butynoyl-O,O,O-(2-naphthoyl) 4-chlorophenylacetyldeferoxamine; and C. N-(3-chloropropionyl)-O,O,O-(4-chloro-2-butenoyl)-4-chlorocyclohexyl-carbonyl)( 4-chlorocyclohexyl-acetyl) deferoxamine; N-(4-chlorocyclohexylcarbonyl)-O,O,O-(4-chloro-2-butenoyl)(3-chloropropionyl)( 4-chlorocyclohexylacetyl)deferoxamine; and N-(4-chlorocyclohexylacetyl )-O,O,O-(4-chlorocyclohexylcarbonyl)(3-chloropropionyl) (4-chloro-2-butenoyl )deferoxamine.

Products A, B and C also include other possible isomers of the groups described therein. Also, the position of the acyl groups on the nitrogen and oxygen is not yet known with certainity.

EXAMPLE 5

Preparation of N-Octanoyl-O,O,O-trihydrogendeferoxamine (Step 2)

(a) N-Octanoyl-O,O,O-trioctanoyldeferoxamine (3.5 g, from Example 4) is dissolved in 250 ml of ether, 100 ml of methanol and saturated at ambient temperature with ammonia gas. After stirring for 3 days (about 72 hr) at ambient temperature, the reaction mixture is evaporated to dryness using reduced pressure, and the solid residue is boiled five times with hexane to remove the octanoic acid amide. The remaining colorless crystalline product is recrystallized from n-propanol/water (66/34) to give 1.5 g of N-octanoyl-O,O,O-trihydrogendeferoxamine, m.p. 185°–187°. The infrared and nuclear magnetic resonance spectra are consistent with this structure. The product is sparingly soluble in water and ordinary organic solvents.

(b) Similarly, proceeding as is described above in Subpart (a) of this Example, but substituting a stoichiometrically equivalent amount of the deferoxamines as prepared in Example 4, Subpart (b) above for N-octanoyl-O,O,O-trioctanoyldeferoxamine, there is obtained the corresponding N-acetyl-O,O,O-trihydrogendeferoxamine;

N-propionyl-O,O,O-trihydrogendeferoxamine;

N-butyryl-O,O,O-trihydrogendeferoxamine;

N-pivalyl-O,O,O-trihydrogendeferoxamine;

N-valeryl-O,O,O-trihydrogendeferoxamine;

N-isovaleryl-O,O,O-trihydrogendeferoxamine;

N-dodecanoyl-O,O,O-trihydrogendeferoxamine;

N-palmitoyl-O,O,O-trihydrogendeferoxamine; or

N-hexacosanoyl-O,O,O-trihydrogendeferoxamine.

(c) Similarly, proceeding as is described above in Subpart (a) of this Example, but substituting a stoichiometrically equivalent amount of the deferoxamines as prepared in Example 4, Subpart (c) above for N-octanoyl-O,O,O-trioctanoyldeferoxamine, there is obtained the corresponding N-(3-chlorobutanoyl)-O,O,O-trihydrogendeferoxamine;

N-(3-chloroisovaleryl)-O,O,O-trihydrogendeferoxamine;

N-(10-chlorooctadecanoyl)-O,O,O-trihydrogendeferoxamine;

N-(10-methoxyoctadecanoyl)-O,O,O-trihydrogendeferoxamine;

N-(9,10-dichlorooctadecanoyl)-O,O,O-trihydrogendeferoxamine;

N-(9,10-dibromooctadecanoyl)-O,O,O-trihydrogendeferoxamine; or

N-(9,10-dimethoxyoctadecanoyl)-O,O,O-trihydrogendeferoxamine.

(d) Similarly, proceeding as is described above in Subpart (a) of this Example, but substituting a stoichiometrically equivalent amount of the deferoxamines as prepared in Example 4, Subpart (d) above for N-octanoyl-O,O,O-trioctanoyldeferoxamine, there is obtained the corresponding N-acryloyl-O,O,O-trihydrogendeferoxamine;

N-2-butenoyl-O,O,O-trihydrogendeferoxamine;

N-2-pentenoyl-O,O,O-trihydrogendeferoxamine;

N-2-octenoyl-O,O,O-trihydrogendeferoxamine;

N-2-oleoyl-O,O,O-trihydrogendeferoxamine; or

N-2-pentacosenoyl-O,O,O-trihydrogendeferoxamine.

(e) Similarly, proceeding as is described above in Subpart (a) of this Example, but substituting a stoichiometrically equivalent amount of the deferoxamines as prepared in Example 4, Subpart (e) above for N-octanoyl-O,O,O-trioctanoyldeferoxamine, there is obtained the corresponding N-(2-chloroacryloyl)-O,O,O-trihydrogendeferoxamine;

N-(2-chloropropenoyl)-O,O,O-trihydrogendeferoxamine;

N-(4-methoxybutenoyl)-O,O,O-trihydrogendeferoxamine

N-(2-chlorooctenoyl)-O,O,O-trihydrogendeferoxamine; or

N-(2-chloropentacosenoyl)-O,O,O-trihydrogendeferoxamine.

(f) Similarily, proceeding as is described above in Subpart (a) of this Example, but substituting a stoichiometrically equivalent amount of the deferoxamines as prepared in Example 4, Subpart (e) above for N-octanoyl-O,O,O-trioctanoyldeferoxamine, there is obtained the corresponding N-cyclopropylacetyl-O,O,O-trihydrogendeferoxamine;

N-cyclobutylacetyl-O,O,O-trihydrogendeferoxamine;

N-cyclohexylpropanoyl-O,O,O-trihydrogendeferoxamine;

N-cyclodecyldecanoyl-O,O,O-trihydrogendeferoxamine; or

N-(cyclopentacosanylacetyl)-O,O,O-trihydrogendeferoxamine.

(g) Similarly, proceeding as is described above in Subpart (a) of this Example, but substituting a stoichiometrically equivalent amount of the deferoxamines as prepared in Example 4, Subpart (g) above for N-octanoyl-O,O,O-trioctanoyldeferoxamine, there is obtained the corresponding N-(2-chlorocyclopropylacetyl)-O,O,O-trihydrogendeferoxamine;

N-(4-chlorocyclohexylacetyl)-O,O,O-trihydrogendeferoxamine:

N-(2-chlorocyclopentadecylacetyl)-O,O,O-trihydrogendeferoxamine; or

N-[10-(2-chloropentacosanyl)decanoyl]-O,O,O-trihydrogendeferoxamine.

(h) Similarly, proceeding as is described above in Subpart (a) of this Example, but substituting a stoichiometrically equivalent amount of the deferoxamines as prepared in Example 4, Subpart (h) above for N-octanoyl-O,O,O,-trioctanoyldeferoxamine, there is obtained the corresponding N-(propynoyl)-O,O,O-trihydrogendeferoxamine;

N-(2-hexynoyl)-O,O,O-trihydrogendeferoxamine

N-(2-decynoyl)-O,O,O-trihydrogendeferoxamine; or

N-(2-pentacosynoyl)-O,O,O-trihydrogendeferoxamine.

(i) Similarly, proceeding as is described above in Subpart (a) of this Example, but substituting a stoichiometrically equivalent amount of the deferoxamines as prepared in Example 4, Subpart (i) above for N-octanoyl-O,O,O-trioctanoyldeferoxamine, there is obtained the corresponding N-(4-chloro-2-butynoyl)-O,O,O-trihydrogendeferoxamine (10-chloro-2-decynoyl)-O,O,O-trihydrogen-deferoxamine (15-chloro-3-pentadecynoyl)trihydrogendeferoxamine or (25-chloro-2-pentacosynoyl)-O,O,O-trihydrogendeferoxamine.

(j) Similarly, proceeding as is described above in Subpart (a) of this Example, but substituting a stoichiometrically equivalent amount of the deferoxamines as prepared in Example 4, Subpart (j) above for N-octanoyl-O,O,O-trioctanoyldeferoxamine, there is obtained the corresponding N-benzoyl-O,O,O-trihydrogende feroxamine;

N-(2-naphthoyl)-O,O,O-trihydrogendeferoxamine; or

N-(1-phenanthroyl)-O,O,O-trihydrogendeferoxamine.

(k) Similarly, proceeding as is described above in Subpart (a) of this Example, but substituting a stoichiometrically equivalent amount of the deferoxamines as prepared in Example 4, Subpart (k) above for N-octanoyl-O,O,O-trioctanoyldeferoxamine, there is obtained the corresponding N-(4-chlorobenzoyl)-O,O,O-trihydrogendeferoxamine;

N-(6-methoxy-2-naphthoyl)-O,O,O-trihydrogendeferoxamine; or

N-(6-chloro-1-phenanthroyl)-O,O,O-trihydrogendeferoxamine.

(l) Similarly, proceeding as is described above in Subpart (a) of this Example, but substituting a stoichiometrically equivalent amount of the deferoxamines as prepared in Example 4, Subpart (l) above for N-octanoyl-O,O,O-trioctanoyldeferoxamine, there is obtained the corresponding N-(phenylacetyl)-O,O,O-trihydrogendeferoxamine;

N-(10-phenyldecanoyl)-O,O,O-trihydrogendeferoxamine; or

N-[10-(2-naphthyl)decanoyl]-O,O,O-trihydrogendeferoxamine.

EXAMPLE 6

Preparation of N-Octanoyl-O,O,O-tributyryldeferoxamine (Step 3)

(a) N-Octanoyl-O,O,O-trihydrogen deferoxamine [1.5g, from Example 5(a)] is suspended in a solution of 50 ml of water and 50 ml of chloroform. The well-agitated suspension is adjusted to pH of 9 using 5N sodium hydroxide solution. To this mixture is added dropwise, a solution of 1.4 g of butyryl chloride in 30 ml of chloroform. The pH of 9 of the mixture is maintained by the addition of a 5N sodium hydroxide solution as needed. After 20 ml of the butyryl chloride solution are added, 25 ml of water and 100 ml of chloroform are added to facilitate the mixing of the solution. After the butyryl chloride solution is all added, the reaction mixture is stirred for 2 hours, with periodic adjustment to maintain a pH of 9. The reaction mixture is then diluted with 50 ml of water and 200 ml of chloroform and centrifuged to separate the phases. Any white solid at the interface is removed and discarded. The chloroform phase is washed twice with 100 ml of saturated sodium bicarbonate solution and twice with 100 ml of saturated sodium chloride solution, dried using anhydrous sodium sulfate, filtered and reduced to dryness using reduced pressure. About 2.0 g of a crude waxy white solid is obtained, which is washed twice with ether and recrystallized from 60% ethanol. The solid is air dried to produce 1.1g of N-octanoyl-O,O,O-tributyryldeferoxamine. The infrared and nuclear magnetic resonance spectra are consistent with this structure.

(b) Similarly, proceeding as is described above in Subpart (a) of this Example, but substituting a stoichiometrically equivalent amount of the deferoxamines as prepared in Example 5, Subpart (b) above for N-octanoyl-O,O,O-trihydrogendeferoxamine, there is obtained the corresponding N-acetyl-O,O,O-tributyryldeferoxamine;

N-Propionyl-O,O,O-tributyryldeferoxamine;

N-butyryl-O,O,O-tributyryldeferoxamine;

N-Pivalyl-O,O,O-tributyryldeferoxamine;

N-valeryl-O,O,O-tributyryldeferoxamine;

N-isovaleryl-O,O,O-tributyryldeferoxamine;

N-dodecanoyl-O,O,O-tributyryldeferoxamine;

N-palmitoyl-O,O,O-tributyryldeferoxamine; or

N-hexacosanoyl-O,O,O-tributyryldeferoxamine.

(c) Similarly, proceeding as is described above in Subpart (a) of this Example, but substituting a stoichiometrically equivalent amount of the deferoxamines as prepared in Example 5, Subpart (c) above for N-octanoyl-O,O,O-trihydrogendeferoxamine, there is obtained the corresponding N-3-chlorobutanoyl)-O,O,O-tributyryldeferoxamine N-3-chloroisovaleryl)-O,O,O-tributyryldeferoxamine N-(10-chlorooctadecanoyl)-O,O,O-tributyryldeferoxamine N-(10-methoxyoctadecanoyl)-O,O,O-tributyryldeferoxamine N-(9,10-dichlorooctadecanoyl)-O,O,O-tributyryldeferoxamine;

N-(9,10-dibromooctadecanoyl)-O,O,O-tributyryldeferoxamine; or

N-(9,10-dimethoxyoctadecanoyl)-O,O,O-tributyryldeferoxamine.

(d) Similarly, proceeding as is described above in Subpart (a) of this Example, but substituting a stoichiometrically equivalent amount of the deferoxamines as prepared in Example 5, Subpart (d) above for N-octanoyl-O,O,O-trihydrogendeferoxamine, there is obtained the corresponding N-acryloyl-O,O,O-tributyryldeferoxamine;

N-2-butenoyl-O,O,O-tributyryldeferoxamine;

N-2-pentenoyl-O,O,O-tributyryldeferoxamine;

N-2-octenoyl-O,O,O-tributyryldeferoxamine;

N-2-oleoyl-O,O,O-tributyryldeferoxamine; or

N-2-pentacosenoyl-O,O,O-tributyryldeferoxamine.

(e) Similarly, proceeding as is described above in Subpart (a) of this Example, but substituting a stoichiometrically equivalent amount of the deferoxamines as prepared in Example 5, Subpart (e) above for N-octanoyl-O,O,O-trihydrogendeferoxamine, there is obtained the corresponding N-2-chloroacryloyl-O,O,O-tributyryldeferoxamine N-(2-chloropropenoyl)-O,O,O-tributyryldeferoxamine N-(4-methoxybutenoyl)-O,O,O-tributyryldeferoxamine N-(2-chlorooctenoyl)-O,O,O-tributyryldeferoxamine; or N(2-chloropentacosenoyl)-O,O,O-tributyryldeferoxamine.

(f) Similarly, proceeding as is described above in Subpart (a) of this Example, but substituting a stoichiometrically equivalent amount of the deferoxamines as prepared in Example 5, Subpart (f) above for N-octanoyl-O,O,O-trihydrogendeferoxamine, there is obtained the corresponding N-cyclopropylacetyl-O,O,O-tributyryldeferoxamine;

N-cyclobutylacetyl-O,O,O-tributyryldeferoxamine;

N-cyclohexylpropanoyl-O,O,O-tributyryldeferoxamine;

N-[10-(cyclodecyl)decanoyl]-O,O,O-tributyryldeferoxamine; or

N-(cyclopentacosanylacetyl)-O,O,O-tributyryldeferoxamine.

(g) Similarly, proceeding as is described above in Subpart (a) of this Example, but substituting a stoichiometrically equivalent amount of the deferoxamines as prepared in Example 5, Subpart (g) above for N-octanoyl-O,O,O-trihydrogendeferoxamine, there is obtained the corresponding N-(2-chlorocyclopropylacetyl)-O,O,O-tributyryldeferoxamine;

N-(4-chlorocyclohexylacetyl)-O,O,O-tributyryldeferoxamine;

N-(2-chloropentadecylacetyl)-O,O,O-tributyryldeferoxamine; or

N-[10-(2-chloropentacosanyl)decanoyl]-O,O,O-tributyryldeferoxamine.

(h) Similarly, proceeding as is described above in Subpart (a) of this Example, but substituting a stoichiometrically equivalent amount of the deferoxamines as prepared in Example 5, Subpart (h) above for N-octanoyl-O,O,O-trihydrogendeferoxamine, there is obtained the corresponding N-(propynoyl)-O,O,O-tributyryldeferoxamine;

N-(2-hexynoyl)-O,O,O-tributyryldeferoxamine:

N-(2-decynoyl)-O,O,O-tributyryldeferoxamine; or

N-(2-pentacosynoyl)-O,O,O-tributyryldeferoxamine.

(i) Similarily, proceding as is described above in Subpart (a) of this Example, but substituting a stoichiometrically equivalent amount of the deferoxamines as prepared in Example 5, Subpart (i) above for N-octanoyl-O,O,O-trihydrogendeferoxamine, there is obtained the corresponding N-(4-chloro-2-butynoyl)-O,O,O-tributyryldeferoxamine N-(10-chloro-2-decynoyl)-O,O,O-tributyryldeferoxamine N-(15-chloro-3-pentadecynoyl)-O,O,O-tributyryldeferoxamine; or N-(25-chloro-2-pentacosynoyl)-O,O,O-tributyryldeferoxamine (j) Similarily, proceeding as is described above in Subpart (a) of this Example, but substituting a stoichiometrically equivalent amount of the deferoxamines as prepared in Example 5, Subpart (j) above for N-octanoyl-O,O,O-trihydrogendeferoxamine, there is obtained the corresponding N-benzoyl-O,O,O-tributyryldeferoxamine;

N-(2-naphthoyl)-O,O,O-tributyryldeferoxamine; or

N-(1-phenanthroyl)-O,O,O-tributyryldeferoxamine.

(k) Similarily, proceeding as is described above in Subpart (a) of this Example, but substituting a stoichiometrically equivalent amount of the deferoxamines as prepared in Example 5, Subpart (k) above for N-octanoyl-O,O,O-trihydrogendeferoxamine, there is obtained the corresponding N-(4-chlorobenzoyl)-O,O,O-tributyryldeferoxamine (6-methoxy-2-naphthoyl)-O,O,O-tributyryldeferoxamine N-(6-chloro-1-phenanthroyl)-O,O,O-tributyryldeferoxamine.

(1) Similarily, proceeding as is described above in Subpart (a) of this Example, but substituting a stoichiometrically equivalent amount of the deferoxamines as prepared in Example 5, Subpart (1) above for N-octanoyl-O,O,O-trihydrogendeferoxamine, there is obtained the corresponding N-(phenylacetyl)-O,O,O-tributyryldeferoxamine;

N-(10-phenyldecanoyl)-O,O,O-tributyryldeferoxamine; or

N-(2-naphthyldecanoyl)-O,O,O-tributyryldeferoxamine.

(m) Similarily, proceeding as is described above in Subpart (a) of this example, but substituting one half of the stoichiometrically equivalent amount of the following equimolar mixtures of acyl chlorides:

A. acetyl chloride, butyryl chloride, and acryloyl chloride;

B. octanoyl chloride and acryloylchloride; or

C. butyryl chloride and octanoyl chloride for butyryl chloride, there is obtained a corresponding mixture of products including:

N-octanoyl-O,O,O-acetylbutyrylacryloyldeferoxamine;

N-octanoyl-O,O,O-hydrogenacryloylacetyldeferoxamine; or N-octanoyl-O,O,O-butyrylacryloylhydrogendeferoxamine;

B. N-octanoyl-O,O,O-octanoylhydrogenacryloyldeferoxamine;

N-octanoyl-O,O,O-octanoylacryloylhydrogendeferoxamine; or

N-octanoyl-O,O,O-dioctanoylacryloyldeferoxamine; and

C. N-octanoyl-O,O,O-butyryloctanoylhydrogendeferoxamine;

N-octanoyl-O,O,O-octanoylhydrogenbutyryldeferoxamine; or

N-octanoyl-O,O,O-hydrogenbutyryldeferoxamine.
The exact positions of the acyl or hydrogen groups has not yet been established with certainty.

In Examples 7 and 8, the active ingredient is N-acetyl-O,O,O-trioctanoyldeferoxamine. Other compounds of formula I may be substituted therein. These include those compounds where $R_1$ is lower acyl, $R_2$, $R_3$ and $R_4$ are acyl ($R_5$ is lower alkyl) and $R_6$, $R_7$ and $R_8$ are hydrogen, and compounds where $R_1$ is acyl ($R_5$ is lower alkyl), $R_2$, $R_3$ and $R_4$ are acyl ($R_5$ is lower alkyl) and of $R_6$, $R_7$ and $R_8$, two are hydrogen and the remaining one is acyl ($R_5$ is lower alkyl). Preferred is N-acetyl-O,O,O,N,H,H-tetraoctanoyldeferoxamine.

EXAMPLE 7

Tablet Formation

| Ingredients | Quantity per Tablet, mgs. |
|---|---|
| Active Ingredient | 350 |
| Cornstarch | 20 |
| Lactose, spray dried | 100 |
| Magnesium stearate | 2 |

The above ingredients are thoroughly mixed, granulated, and pressed into single scored tablets.

EXAMPLE 8

Capsule Formation

| Ingredients | Quantity per Capsule, mgs. |
|---|---|
| Active Ingredient | 350 |
| Lactose, spray dried | 100 |
| Magnesium stearate | 2 |

The above ingredients are mixed and introduced into a hard-shell gelatin capsule.

While the present invention has been described with reference to the specific embodiments thereof, it should be understood by those skilled in this art that various changes may be made and equivalents may be substituted without departing from the true spirit and scope of the present invention. In addition, many modifications may be made to adapt a particular situation, material, or composition of matter, process, process step or steps, or the present objective to the spirit and scope of this invention, without departing from its essential teachings.

I claim:

1. A pharmaceutical composition for oral administration to a mammal to treat and reduce a metal ion overload condition, by administering a compound of the structure:

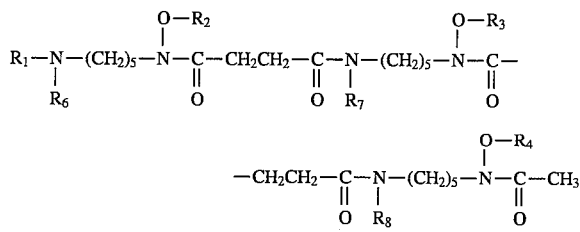

wherein $R_6$, $R_7$ and $R_8$ are each —H, and $R_1$ is selected from —(C=O)-$R_5$ wherein $R_5$ is selected from alkyl groups having from 2 to 13 carbon atoms, $R_2$, $R_3$ and $R_4$ are each independently selected from acyl group —(C=O)-$R_{5a}$ where $R_{5a}$ is selected from alkyl groups having from 2 to 4 carbon atoms, or the pharmaceutically acceptable non-toxic salt or ester thereof, optimally, in a pharmaceutically acceptable excipient.

2. The pharmaceutical composition of claim 1 wherein $R_1$, $R_2$, $R_3$ and $R_4$ are each selected from identical acyl groups.

3. The pharmaceutical composition of claim 2 wherein in groups $R_5$ and $R_{5a}$ the alkyl group has 2 carbon atoms, ethyl.

4. The pharmaceutical composition of claim 2 wherein in groups $R_5$ and $R_{5a}$ the alkyl group has 3 carbon atoms, n-propyl or isopropyl.

5. The pharmaceutical composition of claim 2 wherein in groups $R_5$ and $R_{5a}$ the alkyl group has 4 carbon atoms, n-butyl, isobutyl sec-butyl or tert-butyl.

6. The pharmaceutical composition of claim 2 wherein in groups $R_5$ and $R_{5a}$ the alkyl group has 5 carbon atoms, n-pentyl or isopentyl.

7. The pharmaceutical composition of claim 2 wherein in groups $R_5$ and $R_{5a}$ the alkyl group has 6 carbon atoms, n-hexyl and isohexyl.

8. The pharmaceutical composition of claim 1 wherein the ion is selected from iron$^{+3}$ or aluminum$^{+3}$.

9. A pharmaceutical composition of the structure:

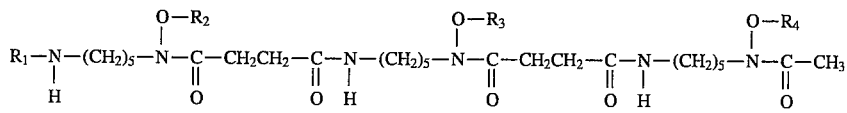

wherein $R_1$ is myristoyl $R_2$, $R_3$ and $R_4$ are each acyl groups wherein the acyl group is propionyl.

10. The pharmaceutical composition of claim 9 wherein the ion is selected from iron or aluminum and the effective oral dosage for a human being is between about 25 and 200 mg/kg/day.

11. The pharmaceutical composition of claim 1 wherein the effective oral dosage for a human being is between about 25 and 200 mg/kg/day.

12. The pharmaceutical composition of claim 5 wherein the ion is selected from iron or aluminum and the effective oral dosage for a human being is between about 25 and 200 mg/kg/day.

13. A pharmaceutical composition for treating an ion overload condition in a human being which comprises a therapeutically effective amount of a compound of the formula:

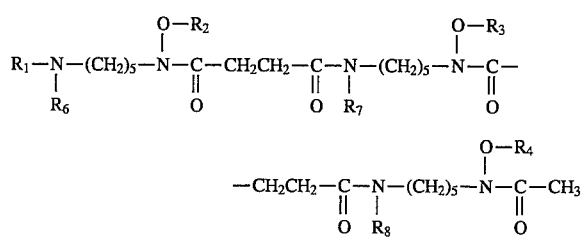

wherein:

R₁ is acyl of the formula: —(C=O)-R₅; and R₂, R₃, R₄, R₆, R₇ and R₈ are independently selected from the group consisting of hydrogen, and acyl of the formula —C(=O)-R₅, wherein R₅ is selected from the groups of alkyls, substituted alkyls, alkenyls, substituted alkenyls, cycloalkyls, substituted cycloalkyls, alkylene cycloalkyls, alkylene substituted cycloalkyls, alkynyls, substituted alkynyls, aryls substituted aryls, arylalkylenes and substituted arylalkylenes, wherein at least one of R₂, R₃, and R₄ is acyl of the formula —C(=O)-R₅ in admixture with a pharmaceutically acceptable excipient.

14. The composition of claim 13 wherein in R₁, R₅ is alkyl; and R₂, R₃, R₄, R₆, R₇ and R₈ are independently selected from hydrogen and acyls of the formula —(G=O)-R₅ wherein R₅ is independently selected from alkyl groups.

15. The composition of claim 14 wherein in R₁, the alkyl groups are lower alkyl groups; and R₂, R₃, R₄, R₆, R₇ and R₈, are independently selected from hydrogen and acyl wherein the alkyl groups are lower alkyl groups.

* * * * *